US012637699B2

(12) United States Patent
Deinhammer et al.

(10) Patent No.: US 12,637,699 B2
(45) Date of Patent: May 26, 2026

(54) PROCESSES FOR PRODUCING FERMENTATION PRODUCTS

(71) Applicant: Novozymes A/S, Bagsvaerd (DK)

(72) Inventors: Randall Scott Deinhammer, Wake Forest, NC (US); Joyce Craig, Pittsboro, NC (US); Suzanne Clark, Youngsville, NC (US); John Matthews, Louisburg, NC (US); Anne Glud Hjulmand, Bagsvaerd (DK); Chee-Leong Soong, Raleigh, NC (US); Zhengfang Kang, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 18/637,805

(22) Filed: Apr. 17, 2024

(65) Prior Publication Data

US 2024/0271167 A1 Aug. 15, 2024

Related U.S. Application Data

(60) Continuation of application No. 17/229,246, filed on Apr. 13, 2021, now Pat. No. 11,987,831, which is a continuation of application No. 16/702,746, filed on Dec. 4, 2019, now abandoned, which is a division of application No. 15/961,269, filed on Apr. 24, 2018, now Pat. No. 10,526,620, which is a division of application No. 14/648,477, filed as application No. PCT/US2013/071982 on Nov. 26, 2013, now Pat. No. 10,227,613, which is a continuation-in-part of application No. 14/388,595, filed as application No. PCT/US2013/034337 on Mar. 28, 2013, now Pat. No. 9,856,498.

(60) Provisional application No. 61/731,806, filed on Nov. 30, 2012, provisional application No. 61/617,799, filed on Mar. 30, 2012.

(51) Int. Cl.

| | |
|---|---|
| ***C12P 7/06*** | (2006.01) |
| ***C12N 9/26*** | (2006.01) |
| ***C12N 9/28*** | (2006.01) |
| ***C12N 9/44*** | (2006.01) |
| ***C12N 9/52*** | (2006.01) |
| ***C12N 9/58*** | (2006.01) |
| ***C12N 9/62*** | (2006.01) |
| ***C12P 7/08*** | (2006.01) |
| ***C12P 7/14*** | (2006.01) |
| ***C12P 19/14*** | (2006.01) |
| ***C13K 1/06*** | (2006.01) |

(52) U.S. Cl.

CPC .............. *C12P 7/14* (2013.01); *C12N 9/2414* (2013.01); *C12N 9/2417* (2013.01); *C12N 9/2457* (2013.01); *C12N 9/52* (2013.01); *C12N 9/58* (2013.01); *C12N 9/62* (2013.01); *C12P 7/06* (2013.01); *C12P 7/08* (2013.01); *C12P 19/14* (2013.01); *C13K 1/06* (2013.01); *C12P 2201/00* (2013.01); *C12P 2203/00* (2013.01); *Y02E 50/10* (2013.01)

(58) Field of Classification Search

CPC ...... C12P 7/06; C12P 7/14; C12P 7/08; C12P 19/14; C12N 9/52; C12N 9/28; C12N 9/44; C12N 9/62; C12N 9/58; C12N 9/2414

See application file for complete search history.

(56) References Cited

U.S. PATENT DOCUMENTS

| | | | | |
|---|---|---|---|---|
| 5,231,017 | A | 7/1993 | Lantero | |
| 7,541,026 | B2 | 6/2009 | Power | |
| 7,641,928 | B2 | 1/2010 | Jump | |
| 8,338,121 | B2 | 12/2012 | Sweeney | |
| 8,541,651 | B2 | 9/2013 | Wogulis | |
| 8,580,536 | B2 | 11/2013 | Mcbrayer | |
| 9,688,975 | B2 | 6/2017 | Wogulis | |
| 10,233,473 | B2 * | 3/2019 | Shasky | C12P 19/02 |
| 11,987,831 | B2 * | 5/2024 | Deinhammer | C12P 7/06 |
| 2004/0115779 | A1 | 6/2004 | Olsen | |
| 2004/0234649 | A1 | 11/2004 | Lewis | |
| 2005/0100996 | A1 | 5/2005 | Lantero, Jr. | |
| 2011/0008864 | A1 | 1/2011 | Deinhammer | |
| 2011/0039308 | A1 | 2/2011 | Slupska | |
| 2011/0111453 | A1 | 5/2011 | Mcbrayer | |
| 2011/0171674 | A1 | 7/2011 | Lopes-Ferreira | |
| 2012/0034659 | A1 | 2/2012 | Bergsma | |
| 2013/0217079 | A1 | 8/2013 | Wogulis | |
| 2014/0080183 | A1 | 3/2014 | Dieker et al. | |

(Continued)

FOREIGN PATENT DOCUMENTS

| | | |
|---|---|---|
| CA | 1143677 | 3/1983 |
| CN | 102083991 A | 6/2011 |

(Continued)

OTHER PUBLICATIONS

Adav et al, Molecular & Cellular Proteomics, 11.7, pp. 1-15.

(Continued)

*Primary Examiner* — Maryam Monshipouri
(74) *Attorney, Agent, or Firm* — David A. Fazzolare

(57) ABSTRACT

The present invention relates to processes for producing fermentation products from starch-containing material, wherein an alpha-amylase and optionally a thermostable protease, pullulanase and/or glucoamylase are present and/or added during liquefaction, wherein a cellulolytic composition is present and/or added during fermentation or simultaneous saccharification and fermentation. The invention also relates to a composition suitable for use in a process of the invention.

27 Claims, No Drawings

Specification includes a Sequence Listing.

(56) References Cited

U.S. PATENT DOCUMENTS

| | | | | |
|---|---|---|---|---|
| 2015/0218606 | A1 | 8/2015 | Van Brussel-Zwijnen | |
| 2021/0230644 | A1* | 7/2021 | Deinhammer .......... | C12P 19/14 |

FOREIGN PATENT DOCUMENTS

| | | | |
|---|---|---|---|
| EP | 1916308 | A1 | 4/2008 |
| JP | 04004888 | | 1/1992 |
| WO | 92/20777 | A1 | 11/1992 |
| WO | 1997/038111 | A1 | 10/1997 |
| WO | 2001/060752 | A1 | 8/2001 |
| WO | 2001/062947 | A1 | 8/2001 |
| WO | 02/38787 | A2 | 5/2002 |
| WO | 2002/038787 | A2 | 5/2002 |
| WO | 2004/080923 | A2 | 9/2004 |
| WO | 2005/074656 | A2 | 8/2005 |
| WO | 2005/113785 | A2 | 12/2005 |
| WO | 2006017048 | A2 | 2/2006 |
| WO | 2006/086792 | A2 | 8/2006 |
| WO | 2007/056321 | A1 | 5/2007 |
| WO | 2007/076388 | A2 | 7/2007 |
| WO | 2008/023060 | A1 | 2/2008 |
| WO | 2009109119 | A1 | 9/2009 |
| WO | 2009/121058 | A1 | 10/2009 |
| WO | 2009/148945 | A1 | 12/2009 |
| WO | 2010008841 | A2 | 1/2010 |
| WO | 2010/128140 | A1 | 11/2010 |
| WO | 2011/072191 | A2 | 6/2011 |
| WO | 2011/080352 | A1 | 7/2011 |
| WO | 2011/126897 | A2 | 10/2011 |
| WO | 2012/044915 | A2 | 4/2012 |
| WO | 2012088303 | A2 | 6/2012 |
| WO | 2012/109119 | A2 | 8/2012 |
| WO | 2012/149275 | A1 | 11/2012 |
| WO | 2013/148993 | A1 | 10/2013 |
| WO | 2013/166405 | A2 | 11/2013 |
| WO | 2013/181760 | A1 | 12/2013 |
| WO | 2014/028434 | A2 | 2/2014 |
| WO | 2014/092960 | A1 | 6/2014 |
| WO | 2014/093123 | A1 | 6/2014 |
| WO | 2014/093125 | A1 | 6/2014 |
| WO | 2014/099415 | A1 | 6/2014 |
| WO | 2015/035914 | A1 | 3/2015 |
| WO | 2015/065978 | A1 | 5/2015 |

OTHER PUBLICATIONS

Basu et al, 2006, Biochim Biophys Acta, vol. 1760, No. 2, pp. 134-140.

Chung et al, 1985, Biotechnol Bioeng, vol. 27, pp. 308-315.

Fedrova et al, 2010, UniprotKB Accession No. A1CR85.

Fedrova et al, 2010, UniprotKB Accession No. A1D51.

Galand, 1986, Biotechnol Bioeng, vol. 27, pp. 308-315.

Horikoshi et al, 1989, WPI Access No. 1989-304909.

Horikoshi et al, 1992, WPI Access No. 1992-060502.

Juhasz et al, Process Biochemistry, vol. 40, pp. 3519-3525.

Lynd et al, 2002, Microbiol Bol Biol Revsk vol. 66, No. 3, pp. 506-577.

Martinez et al, 2011, UniProt, Accession No. G0RRG0.

Morita, 1987, WPI Access No. 1987-059541.

Soni, 2007, Microbes Section 4-6-5, 336.

Thevelein et al, 1995, Trends Biochem Sci, vol. 20, No. 1, pp. 3-10.

Cao et al., 2006, Chemical Production and Technology 13, 50-53—Incl EnAb.

De Souza et al., 2010, Brazilian Journal of Microbiology 41, 850-861.

Thomas 2009, Washington University in St. Louis,, School of Engineering and Applied Science Department of Energy, Environmental, and Chemical Engineering "Enzymatic Enhancement of Water Removal in the Dry Grind Corn to Ethanol Process" PhD. Thesis.

Wood et al, 1978, J Biochem 171, 61-72.

Kawaguchi et al., 1996, PIR_80 database, Accession No. JC4939.

* cited by examiner

SEQUENCE LISTING

```
Sequence total quantity: 29
SEQ ID NO: 1           moltype = AA  length = 515
FEATURE                Location/Qualifiers
source                 1..515
                       mol_type = protein
                       organism = Bacillus stearothermophilus
SEQUENCE: 1
AAPFNGTMMQ YFEWYLPDDG TLWTKVANEA NNLSSLGITA LWLPPAYKGT SRSDVGYGVY  60
```

-continued

```
DLYDLGEFNQ KGTVRTKYGT KAQYLQAIQA AHAAGMQVYA DVVFDHKGGA DGTEWVDAVE  120
VNPSDRNQEI SGTYQIQAWT KFDFPGRGNT YSSFKWRWYH FDGVDWDESR KLSRIYKFRG  180
IGKAWDWEVD TENGNYDYLM YADLDMDHPE VVTELKNWGK WYVNTTNIDG FRLDAVKHIK  240
FSFFPDWLSY VRSQTGKPLF TVGEYWSYDI NKLHNYITKT NGTMSLFDAP LHNKFYTASK  300
SGGAFDMRTL MTNTLMKDQP TLAVTFVDNH DTEPGQALQS WVDPWFKPLA YAFILTRQEG  360
YPCVFYGDYY GIPQYNIPSL KSKIDPLLIA RRDYAYGTQH DYLDHSDIIG WTREGVTEKP  420
GSGLAALITD GPGGSKWMYV GKQHAGKVFY DLTGNRSDTV TINSDGWGEF KVNGGSVSVW  480
VPRKTTVSTI ARPITTRPWT GEFVRWTEPR LVAWP                            515

SEQ ID NO: 2           moltype = DNA  length = 1068
FEATURE                Location/Qualifiers
misc_feature           58..534
mat_peptide            535..1068
source                 1..1068
                       mol_type = genomic DNA
                       organism = Thermoascus aurantiacus
CDS                    1..1065
SEQUENCE: 2
atgcggctcg ttgcttccct aacggccttg gtggccttgt ccgtacctgt ctttcccgct  60
gctgtcaacg tgaagcgtgc ttcgtcctac ctggagatca ctctgagcca ggtcagcaac  120
actctgatca aggccgtggt ccagaacact ggtagcgacg agttgtcctt cgttcacctg  180
aacttcttca aggaccccgc tcctgtcaaa aaggtatcgg tctatcgcga tgggtctgaa  240
gtgcagttcg agggcatttt gagccgctac aaatcgactg gcctctctcg tgacgccttt  300
acttatctgg ctcccggaga gtccgtcgag gacgtttttg atattgcttc gacttacgat  360
ctgaccagcg gcggccctgt aactatccgt actgagggag ttgttcccta cgccacggct  420
aacagcactg atattgccgg ctacatctca tactcgtcta atgtgttgac cattgatgtc  480
gatggcgccg ctgctgccac tgtctccaag gcaatcactc ctttggaccg ccgcactagg  540
atcagttcct gctccggcag cagacagagc gctcttacta cggctctcag aaacgctgct  600
tctcttgcca acgcagctgc cgacgcggct cagtctggat cagcttcaaa gttcagcgag  660
tacttcaaga ctacttctag ctctacccgc cagaccgtgg ctgcgcgtct tcgggctgtt  720
gcgcgggagg catcttcgtc ttcttcggga gccaccacgt actactgcga cgatccctac  780
ggctactgtt cctccaacgt cctggcttac accctgcctt catacaacat aatcgccaac  840
tgtgacattt tctatactta cctgccggct ctgaccagta cctgtcacgc tcaggatcaa  900
gcgaccactg cccttcacga gttcacccat gcgcctggcg tctacagccc tggcacggac  960
gacctggcgt atggctacca ggctgcgatg ggtctcagca gcagccaggc tgtcatgaac  1020
gctgacacct acgctctcta tgcgaatgcc atataccttg gttgctaa              1068

SEQ ID NO: 3           moltype = AA  length = 355
FEATURE                Location/Qualifiers
source                 1..355
                       mol_type = protein
                       organism = Thermoascus aurantiacus
SEQUENCE: 3
MRLVASLTAL VALSVPVFPA AVNVKRASSY LEITLSQVSN TLIKAVVQNT GSDELSFVHL  60
NFFKDPAPVK KVSVYRDGSE VQFEGILSRY KSTGLSRDAF TYLAPGESVE DVFDIASTYD  120
LTSGGPVTIR TEGVVPYATA NSTDIAGYIS YSSNVLTIDV DGAAAATVSK AITPLDRRTR  180
ISSCSGSRQS ALTTALRNAA SLANAAADAA QSGSASKFSE YFKTTSSSTR QTVAARLRAV  240
AREASSSSSG ATTYYCDDPY GYCSSNVLAY TLPSYNIIAN CDIFYTYLPA LTSTCHAQDQ  300
ATTALHEFTH APGVYSPGTD DLAYGYQAAM GLSSSQAVMN ADTYALYANA IYLGC       355

SEQ ID NO: 4           moltype = DNA  length = 49
FEATURE                Location/Qualifiers
misc_feature           1..49
                       note = Synthetic Construct
source                 1..49
                       mol_type = other DNA
                       organism = synthetic construct
SEQUENCE: 4
aacgacggta cccggggatc ggatccatgc ggctcgttgc ttccctaac             49

SEQ ID NO: 5           moltype = DNA  length = 48
FEATURE                Location/Qualifiers
misc_feature           1..48
                       note = Artificial Construct
source                 1..48
                       mol_type = other DNA
                       organism = synthetic construct
SEQUENCE: 5
ctaattacat gatgcggccc ttaattaatt agcaaccaag gtatatgg              48

SEQ ID NO: 6           moltype = DNA  length = 20
FEATURE                Location/Qualifiers
misc_feature           1..20
                       note = Artificial Construct
source                 1..20
                       mol_type = other DNA
                       organism = synthetic construct
SEQUENCE: 6
taggagttta gtgaacttgc                                             20
```

```
SEQ ID NO: 7           moltype = DNA  length = 18
FEATURE                Location/Qualifiers
misc_feature           1..18
                       note = Artificial Construct
source                 1..18
                       mol_type = other DNA
                       organism = synthetic construct
SEQUENCE: 7
ttcgagcgtc ccaaaacc                                                18

SEQ ID NO: 8           moltype = DNA  length = 1851
FEATURE                Location/Qualifiers
source                 1..1851
                       mol_type = genomic DNA
                       organism = Penicillium oxalicum
CDS                    1..1851
SEQUENCE: 8
atgcgtctca ctctattatc aggtgtagcc ggcgttctct gcgcaggaca gctgacggcg  60
gcgcgtcctg atcccaaggg tgggaatctg acgccgttca tccacaaaga gggcgagcgg  120
tcgctccaag gcatcttgga caatctcggt gggcgaggta agaaaacacc cggcactgcc  180
gcagggttgt ttattgccag tccaaacaca gagaatccaa actattatta tacatggact  240
cgtgactcag ctttgactgc caagtgcttg atcgacctgt tcgaagactc tcgggcaaag  300
tttccaattg accgcaaata cttggaaaca ggaattcggg actacgtgtc gtcccaagca  360
atcctccaga gtgtgtctaa tccttctgga accctgaagg atggctctgg tctgggtgaa  420
cccaagtttg agattgacct gaatcccttt tcgggtgcct ggggtcggcc tcagcgggat  480
ggcccagcgc tgcgagcgac cgctatgatc acctacgcca actacctgat atcccatggt  540
cagaaatcgg atgtgtcaca ggtcatgtgg ccgattattg ccaatgatct agcatatgtt  600
ggtcaatact ggaataatac cggatttgac ctgtgggaag aggtggatgg gtcaagcttt  660
ttcacgattg cggtccagca ccgagccctt gttgaaggct cgcaactggc gaaaaagctc  720
ggcaagtcct gcgatgcctg tgattctcag cctccccaga tattgtgttt cctgcagagt  780
ttctggaacg gaaagtacat cacctccaac atcaacacgc aagcaagccg ctctggtatc  840
gacctggact ctgtcctggg aagcattcat acctttgatc ccgaagcagc ctgtgacgat  900
gcaactttcc agccttgttc tgcccgcgct ctggcgaacc acaaggtcta tgtggattcc  960
ttccgctcta tctacaagat taatgcgggt cttgcagagg gatcggctgc caacgttggc  1020
cgctaccccg aggatgttta ccaaggaggc aatccatggt atctcgccac cctaggcgca  1080
tctgaattgc tttacgacgc cttgtaccag tgggacagac ttggcaaact tgaagtctcg  1140
gagacctcgt tgtcattctt caaagacttt gacgcgaccg tgaaaattgg ctcgtactcg  1200
aggaacagca agacctacaa gaaattgacc cagtccatca agtcgtacgc ggacgggttc  1260
atccagttag tgcagcagta cactccttct aatggatctc tggccgagca atacgatcgc  1320
aatacggctg ctcctctctc tgcaaacgat ctgacttggt catttgcctc tttcttgacg  1380
gctacgcaac gccgcgatgc cgtggttcct ccctcctggg gcgcaaagtc ggcaaacaaa  1440
gtcccaacca cttgttcagc ctcccctgtt gtgggtactt ataaggcgcc cacggcaact  1500
ttctcatcca agactaagtg cgtccccgct aaagatattg tgcctatcac gttctacctg  1560
attgagaaca cttactatgg agagaacgtc ttcatgagtg gcaacattac tgcgctgggt  1620
aactgggacg ccaagaaagg cttcccactc accgcaaacc tctacacgca agatcaaaac  1680
ttgtggttcg ccagtgtcga gttcatccca gcaggcacac cctttgagta caagtactac  1740
aaggtcgagc ccaatggcga tattacttgg gagaagggtc ccaaccgggt gttcgtcgct  1800
cccacgggat gcccagttca gcctcactcc aacgacgtgt ggcagttttg a           1851

SEQ ID NO: 9           moltype = AA  length = 616
FEATURE                Location/Qualifiers
source                 1..616
                       mol_type = protein
                       organism = Penicillium oxalicum
SEQUENCE: 9
MRLTLLSGVA GVLCAGQLTA ARPDPKGGNL TPFIHKEGER SLQGILDNLG GRGKKTPGTA  60
AGLFIASPNT ENPNYYYTWT RDSALTAKCL IDLFEDSRAK FPIDRKYLET GIRDYVSSQA  120
ILQSVSNPSG TLKDGSGLGE PKFEIDLNPF SGAWGRPQRD GPALRATAMI TYANYLISHG  180
QKSDVSQVMW PIIANDLAYV GQYWNNTGFD LWEEVDGSSF FTIAVQHRAL VEGSQLAKKL  240
GKSCDACDSQ PPQILCFLQS FWNGKYITSN INTQASRSGI DLDSVLGSIH TFDPEAACDD  300
ATFQPCSARA LANHKVYVDS FRSIYKINAG LAEGSAANVG RYPEDVYQGG NPWYLATLGA  360
SELLYDALYQ WDRLGKLEVS ETSLSFFKDF DATVKIGSYS RNSKTYKKLT QSIKSYADGF  420
IQLVQQYTPS NGSLAEQYDR NTAAPLSAND LTWSFASFLT ATQRRDAVVP PSWGAKSANK  480
VPTTCSASPV VGTYKAPTAT FSSKTKCVPA KDIVPITFYL IENTYYGENV FMSGNITALG  540
NWDAKKGFPL TANLYTQDQN LWFASVEFIP AGTPFEYKYY KVEPNGDITW EKGPNRVFVA  600
PTGCPVQPHS NDVWQF                                                  616

SEQ ID NO: 10          moltype = DNA  length = 4014
FEATURE                Location/Qualifiers
mat_peptide            82..4014
source                 1..4014
                       mol_type = genomic DNA
                       organism = Thermococcus hydrothermalis
CDS                    1..4011
SEQUENCE: 10
atgaggcggg tggttgccct cttcattgca attttgatgc ttggaagcat cgttggagcg  60
aacgttaaga gcgttggcgc ggcggagccg aagccgctca acgtcataat agtctggcac  120
cagcaccagc cctactacta cgaccctgtc caggacgtct acaccaggcc ctgggtcagg  180
```

-continued ctccacgcgg cgaacaacta ctggaagatg gcccactacc tgagccagta cccggaggtt 240
cacgccacca ttgacctctc gggttcgctg atagcccagc ttgccgacta catgaacggc 300
aagaaggaca cctaccagat aatcaccgag aagatagcca acggggaacc cctcaccgtc 360
gacgagaagt ggttcatgct ccaggcaccg ggagggttct tcgacaacac catcccctgg 420
aacggtgaac cgataaccga ccccaacggc aacccgataa gggacttctg ggaccgctac 480
acggagctga agaacaagat gctcagcgca aaggccaagt acgcaaactt cgtgactgag 540
agccagaagg tcgctgtgac gaacgagttc acagagcagg actacataga cctagcggtt 600
ctcttcaatc tcgcttggat tgactacaat tacatcacga gcacgccgga gttcaaggcc 660
ctctacgaca aggttgacga gggcggctat acaagggcgg acgtcaaaac cgttctcgac 720
gcccagatct ggcttctcaa ccacaccttc gaggagcacg agaagataaa cctcctcctc 780
ggaaacggca acgtcgaggt cacggtcgtt ccctacgccc acccgatagg cccgatactc 840
aacgacttcg gctgggacag cgacttcaac gaccaggtca agaaggccga cgaactgtac 900
aagccgtacc tcggcggcgg caccgcggtt ccaaaaggcg gatgggcggc tgagagcgcc 960
ctcaacgaca aaactctgga gatcctcgcc gagaacggct gggagtgggt catgaccgac 1020
cagatggttc tcggaaagct cggcattgag ggaaccgtcg agaactacca caagccctgg 1080
gtggccgagt tcaacggaaa gaagatatac ctcttcccaa gaaatcacga tctaagtgac 1140
agagttggct ttacctacag cggaatgaac cagcagcagg ccgttgagga cttcgtcaac 1200
gagctcctca agctccagaa gcagaactac gatggctcgc tggtttacgt ggtcacgctc 1260
gacggcgaga accccgtgga gaactacccc tacgacgggg agctcttcct caccgaactc 1320
tacaagaagc tgaccgaact ccaggagcag ggtctcataa gaaccctcac cccgagcgag 1380
tacatccagc tctacggcga caaggccaac aagctcacac ctcggatgat ggagcgcctt 1440
gacctcaccg gagacaacgt taacgccctc ctcaaggccc agagcctcgg cgaactctac 1500
gacatgaccg gcgttaagga ggagatgcag tggcccgaga gcagctggat agacggaacc 1560
ctctccacgt ggataggcga gccccaggag aactacggct ggtactggct ctacatggcc 1620
aggaaggccc ttatggagaa caaggataaa atgagccagg cggactggga gaaggcctac 1680
gagtacctgc tccgcgccga ggcaagcgac tggttctggt ggtacggaag cgaccaggac 1740
agcggccagg actacacctt cgaccgctac ctgaagacct acctctacga gatgtacaag 1800
ctggcaggag tcgagccgcc gagctacctc ttcggcaact acttcccgga cggagagccc 1860
tacaccacga ggggcctggt cggactcaag gacggcgaga tgaagaactt ctccagcatg 1920
tccccgctgg caaagggcgt gagcgtctat ttcgacggcg aggggataca cttcatagtg 1980
aaagggaacc tggacaggtt cgaggtgagc atctgggaga aggatgagcg cgttggcaac 2040
acgttcaccc gcctccaaga gaagccggac gagttgagct atttcatgtt cccattctca 2100
agggacagcg ttggtctcct cataaccaag cacgtcgtgt acgagaacgg aaaggccgag 2160
atatacggcg ccaccgacta cgagaagagc gagaagcttg ggaagccac cgtcaagaac 2220
acgagcgaag gaatcgaagt cgtccttccc tttgactaca tagaaaaccc ctccgacttc 2280
tacttcgctg tctcgacggt caaagatgga gaccttgagg tgataagcac tcctgtggag 2340
ctcaagctcc cgaccgaggt caagggagtc gtcatagccg atataaccga cccagaaggc 2400
gacgaccatg ggcccggaaa ctacacttat ccccacggaca aggtcttcaa gccaggtgtt 2460
ttcgacctcc tccgcttcag gatgctcgaa cagacggaga gctacgtcat ggagttctac 2520
ttcaaggacc taggtggtaa cccgtggaac ggacccaacg gcttcagcct ccagataatc 2580
gaggtctacc tcgacttcaa ggacggtgga aacagttcgg ccattaagat gttccccgac 2640
ggaccgggag ccaacgtcaa cctcgacccc gagcatccat gggacgttgc cttcaggata 2700
gcgggctggg actacggaaa cctcatcatc ctgccgaacg gaacggccat ccagggcgag 2760
atgcagattt ccgcagatcc ggttaagaac gccataatag tcaaggttcc aaagaagtac 2820
atcgccataa acgaggacta cggcctctgg ggagacgtcc tcgtcggctc gcaggacggc 2880
tacggcccgg acaagtggag aacggcggca gtggatgcgg agcagtggaa gcttggaggt 2940
gcggacccgc aggcagtcat aaacggcgtg gccccgcgcg tcattgatga gctggttccg 3000
cagggctttg aaccgaccca ggaggagcag ctgagcagct acgatgcaaa cgacatgaag 3060
ctcgccactg tcaaggcgct gctactcctc aagcagggca tcgttgtgac cgacccggag 3120
ggagacgacc acgggccggg aacgtacacc tatccgacgg acaaagtttt caagcccggt 3180
gttttcgacc tcctcaagtt caaggtgacc gagggaagcg acgactggac gctggagttc 3240
cacttcaaag acctcggtgg aaacccgtgg aacgggccga acggcttcag cctgcagata 3300
atcgaggtat acttcgactt caaggagggc gggaacgtct cggccattaa gatgttcccg 3360
gatgggcccg gaagcaacgt ccgtcttgat ccaaatcacc catgggacct ggcgcttagg 3420
atagccggct gggactacgg aaacctgata attctgcccg acggaaccgc ctaccaaggc 3480
gagatgcaga tttccgcaga tccggttaag aacgccataa tagtcaaggt tccaaagaag 3540
tacctgaaca tatccgacta cggactctac accgccgtca tcgtgggttc ccaagacggg 3600
tacggcccgg acaagtggag gcccgtggcc gctgaggccg agcagtggaa gctcggaggc 3660
gcagaccccc aggcggtcat agacaacctc gtaccaaggg tcgttgatga actcgtgccg 3720
gagggcttca agccaacgca ggaggagcag ctgagcagct acgaccttga gaagaagacc 3780
ctggcgacgg tgctcatggt accgctcgtc aatgggactg gcggcgagga accaacgccg 3840
acggagagcc caacggaaac gacgacaacc acacccagcg aaacaaccac cacaacttca 3900
acgaccaccg gcccaagctc aacgaccacc agcacacccg gcggaggaat ctgcggccca 3960
ggcattatag cgggcctggc cctgataccg ctcctcctca agaggaggaa ctga 4014

SEQ ID NO: 11 moltype = AA length = 1337
FEATURE Location/Qualifiers
source 1..1337
mol_type = protein
organism = Thermococcus hydrothermalis
SEQUENCE: 11
MRRVVALFIA ILMLGSIVGA NVKSVGAAEP KPLNVIIVWH QHQPYYYDPV QDVYTRPWVR 60
LHAANNYWKM AHYLSQYPEV HATIDLSGSL IAQLADYMNG KKDTYQIITE KIANGEPLTV 120
DEKWFMLQAP GGFFDNTIPW NGEPITDPNG NPIRDFWDRY TELKNKMLSA KAKYANFVTE 180
SQKVAVTNEF TEQDYIDLAV LFNLAWIDYN YITSTPEFKA LYDKVDEGGY TRADVKTVLD 240
AQIWLLNHTF EEHEKINLLL GNGNVEVTVV PYAHPIGPIL NDFGWDSDFN DQVKKADELY 300
KPYLGGGTAV PKGGWAAESA LNDKTLEILA ENGWEWVMTD QMVLGKLGIE GTVENYHKPW 360
VAEFNGKKIY LFPRNHDLSD RVGFTYSGMN QQQAVEDFVN ELLKLQKQNY DGSLVYVVTL 420
DGENPVENYP YDGELFLTEL YKKLTELQEQ GLIRTLTPSE YIQLYGDKAN KLTPRMMERL 480

-continued

```
DLTGDNVNAL LKAQSLGELY DMTGVKEEMQ WPESSWIDGT LSTWIGEPQE NYGWYWLYMA  540
RKALMENKDK MSQADWEKAY EYLLRAEASD WFWWYGSDQD SGQDYTFDRY LKTYLYEMYK  600
LAGVEPPSYL FGNYFPDGEP YTTRGLVGLK DGEMKNFSSM SPLAKGVSVY FDGEGIHFIV  660
KGNLDRFEVS IWEKDERVGN TFTRLQEKPD ELSYFMFPFS RDSVGLLITK HVVYENGKAE  720
IYGATDYEKS EKLGEATVKN TSEGIEVVLP FDYIENPSDF YFAVSTVKDG DLEVISTPVE  780
LKLPTEVKGV VIADITDPEG DDHGPGNYTY PTDKVFKPGV FDLLRFRMLE QTESYVMEFY  840
FKDLGGNPWN GPNGFSLQII EVYLDFKDGG NSSAIKMFPD GPGANVNLDP EHPWDVAFRI  900
AGWDYGNLII LPNGTAIQGE MQISADPVKN AIIVKVPKKY IAINEDYGLW GDVLVGSQDG  960
YGPDKWRTAA VDAEQWKLGG ADPQAVINGV APRVIDELVP QGFEPTQEEQ LSSYDANDMK  1020
LATVKALLLL KQGIVVTDPE GDDHGPGTYT YPTDKVFKPG VFDLLKFKVT EGSDDWTLEF  1080
HFKDLGGNPW NGPNGFSLQI IEVYFDFKEG GNVSAIKMFP DGPGSNVRLD PNHPWDLALR  1140
IAGWDYGNLI ILPDGTAYQG EMQISADPVK NAIIVKVPKK YLNISDYGLY TAVIVGSQDG  1200
YGPDKWRPVA AEAEQWKLGG ADPQAVIDNL VPRVVDELVP EGFKPTQEEQ LSSYDLEKKT  1260
LATVLMVPLV NGTGGEEPTP TESPTETTTT TPSETTTTTS TTTGPSSTTT STPGGGICGP  1320
GIIAGLALIP LLLKRRN                                                 1337

SEQ ID NO: 12          moltype = AA  length = 809
FEATURE                Location/Qualifiers
REGION                 1..809
                       note = Hybrid pullulanase of Thermoccus hydrothermalis and
                        Thermococcus litoralis
SIGNAL                 1..27
source                 1..809
                       mol_type = protein
                       organism = synthetic construct
SEQUENCE: 12
MKKPLGKIVA STALLISVAF SSSIASAEEP KPLNVIIVWH QHQPYYYDPI QDIYTRPWVR  60
LHAANNYWKM ANYLSKYPDV HVAIDLSGSL IAQLADYMNG KKDTYQIVTE KIANGEPLTL  120
EDKWFMLQAP GGFFDHTIPW NGEPVADENG NPYREQWDRY AELKDKRNNA FKKYANLPLN  180
EQKVKITAEF TEQDYIDLAV LFNLAWIDYN YIINTPELKA LYDKVDVGGY TKEDVATVLK  240
HQMWLLNHTF EEHEKINYLL GNGNVEVTVV PYAHPIGPLL NDFGWYEDFD AHVKKAHELY  300
KKYLGDNRVE PQGGWAAESA LNDKTLEILT NNGWKWVMTD QMVLDILGIP NTVENYYKPW  360
VAEFNGKKIY LFPRNHDLSD RVGFRYSGMN QYQAVEDFVN ELLKVQKENY DGSLVYVVTL  420
DGENPWEHYP FDGKIFLEEL YKKLTELQKQ GLIRTVTPSE YIQMYGDKAN KLTPRMMERL  480
DLTGDNVNAL LKAQSLGELY DMTGVKEEMQ WPESSWIDGT LSTWIGEPQE NYGWYWLYMA  540
RKALMENKDK MSQADWEKAY EYLLRAEASD WFWWYGSDQD SGQDYTFDRY LKTYLYEMYK  600
LAGVEPPSYL FGNYFPDGEP YTTRGLVGLK DGEMKNFSSM SPLAKGVSVY FDGEGIHFIV  660
KGNLDRFEVS IWEKDERVGN TFTRLQEKPD ELSYFMFPFS RDSVGLLITK HVVYENGKAE  720
IYGATDYEKS EKLGEATVKN TSEGIEVVLP FDYIENPSDF YFAVSTVKDG DLEVISTPVE  780
LKLPTEVKGV VIADITDPEG DDHGPGNYT                                    809

SEQ ID NO: 13          moltype = AA  length = 412
FEATURE                Location/Qualifiers
REGION                 1..412
                       note = mat_peptide - Pyrococcus furiosus protease (Pfu)
source                 1..412
                       mol_type = protein
                       organism = Pyrococcus furiosus
SEQUENCE: 13
AELEGLDESA AQVMATYVWN LGYDGSGITI GIIDTGIDAS HPDLQGKVIG WVDFVNGRSY  60
PYDDHGHGTH VASIAAGTGA ASNGKYKGMA PGAKLAGIKV LGADGSGSIS TIIKGVEWAV  120
DNKDKYGIKV INLSLGSSQS SDGTDALSQA VNAAWDAGLV VVVAAGNSGP NKYTIGSPAA  180
ASKVITVGAV DKYDVITSFS SRGPTADGRL KPEVVAPGNW IIAARASGTS MGQPINDYYT  240
AAPGTSMATP HVAGIAALLL QAHPSWTPDK VKTALIETAD IVKPDEIADI AYGAGRVNAY  300
KAINYDNYAK LVFTGYVANK GSQTHQFVIS GASFVTATLY WDNANSDLDL YLYDPNGNQV  360
DYSYTAYYGF EKVGYYNPTD GTWTIKVVSY SGSANYQVDV VSDGSLSQPG SS          412

SEQ ID NO: 14          moltype = AA  length = 595
FEATURE                Location/Qualifiers
REGION                 1..595
                       note = mat_peptide - mature Penicillium oxalicum
                        glucoamylase sequence
source                 1..595
                       mol_type = protein
                       organism = Penicillium oxalicum
SEQUENCE: 14
RPDPKGGNLT PFIHKEGERS LQGILDNLGG RGKKTPGTAA GLFIASPNTE NPNYYYTWTR  60
DSALTAKCLI DLFEDSRAKF PIDRKYLETG IRDYKSSQAI LQSVSNPSGT LKDGSGLGEP  120
KFEIDLNPFS GAWGRPQRDG PALRATAMIT YANYLISHGQ KSDVSQVMWP IIANDLAYVG  180
QYWNNTGFDL WEEVDGSSFF TIAVQHRALV EGSQLAKKLG KSCDACDSQP PQILCFLQSF  240
WNGKYITSNI NTQASRSGID LDSVLGSIHT FDPEAACDDA TFQPCSARAL ANHKVYVDSF  300
RSIYKINAGL AEGSAANVGR YPEDVYQGGN PWYLATLGAS ELLYDALYQW DRLGKLEVSE  360
TSLSFFKDFD ATVKIGSYSR NSKTYKKLTQ SIKSYADGFI QLVQQYTPSN GSLAEQYDRN  420
TAAPLSANDL TWSFASFLTA TQRRDAVVPP SWGAKSANKV PTTCSASPVV GTYKAPTATF  480
SSKTKCVPAK DIVPITFYLI ENTYYGENVF MSGNITALGN WDAKKGFPLT ANLYTQDQNL  540
WFASVEFIPA GTPFEYKYYK VEPNGDITWE KGPNRVFVAP TGCPVQPHSN DVWQF        595

SEQ ID NO: 15          moltype = DNA  length = 25
FEATURE                Location/Qualifiers
```

```
misc_feature           1..25
                       note = Sense Primer
source                 1..25
                       mol_type = other DNA
                       organism = synthetic construct
SEQUENCE: 15
atgcgtctca ctctattatc aggtg                                   25

SEQ ID NO: 16          moltype = DNA  length = 39
FEATURE                Location/Qualifiers
misc_feature           1..39
                       note = Primer F
source                 1..39
                       mol_type = other DNA
                       organism = synthetic construct
SEQUENCE: 16
acacaactgg ggatccacca tgcgtctcac tctattatc                    39

SEQ ID NO: 17          moltype = DNA  length = 37
FEATURE                Location/Qualifiers
misc_feature           1..37
                       note = Primer R
source                 1..37
                       mol_type = other DNA
                       organism = synthetic construct
SEQUENCE: 17
agatctcgag aagcttaaaa ctgccacacg tcgttgg                      37

SEQ ID NO: 18          moltype = DNA  length = 18
FEATURE                Location/Qualifiers
misc_feature           1..18
                       note = Primer K79V F 18mer
source                 1..18
                       mol_type = other DNA
                       organism = synthetic construct
SEQUENCE: 18
gcagtctttc caattgac                                           18

SEQ ID NO: 19          moltype = DNA  length = 18
FEATURE                Location/Qualifiers
misc_feature           1..18
                       note = Primer K79V R 18mer
source                 1..18
                       mol_type = other DNA
                       organism = synthetic construct
SEQUENCE: 19
aattggaaag actgcccg                                           18

SEQ ID NO: 20          moltype = DNA  length = 39
FEATURE                Location/Qualifiers
misc_feature           1..39
                       note = Primer F-NP003940
source                 1..39
                       mol_type = other DNA
                       organism = synthetic construct
SEQUENCE: 20
acacaactgg ggatccacca tgcgtctcac tctattatc                    39

SEQ ID NO: 21          moltype = DNA  length = 37
FEATURE                Location/Qualifiers
misc_feature           1..37
                       note = Primer F-NP003940
source                 1..37
                       mol_type = other DNA
                       organism = synthetic construct
SEQUENCE: 21
agatctcgag aagcttaaaa ctgccacacg tcgttgg                      37

SEQ ID NO: 22          moltype = AA  length = 863
FEATURE                Location/Qualifiers
source                 1..863
                       mol_type = protein
                       organism = Aspergillus fumigatus
SEQUENCE: 22
MRFGWLEVAA LTAASVANAQ ELAFSPPFYP SPWADGQGEW ADAHRRAVEI VSQMTLAEKV  60
NLTTGTGWEM DRCVGQTGSV PRLGINWGLC GQDSPLGIRF SDLNSAFPAG TNVAATWDKT  120
LAYLRGKAMG EEFNDKGVDI LLGPAAGPLG KYPDGGRIWE GFSPDPVLTG VLFAETIKGI  180
QDAGVIATAK HYILNEQEHF RQVGEAQGYG YNITETISSN VDDKTMHELY LWPFADAVRA  240
GVGAVMCSYN QINNSYGCQN SQTLNKLLKA ELGFQGFVMS DWSAHHSGVG AALAGLDMSM  300
```

-continued

```
PGDISFDDGL SFWGTNLTVS VLNGTVPAWR VDDMAVRIMT AYYKVGRDRL RIPPNFSSWT  360
RDEYGWEHSA VSEGAWTKVN DFVNVQRSHS QIIREIGAAS TVLLKNTGAL PLTGKEVKVG  420
VLGEDAGSNP WGANGCPDRG CDNGTLAMAW GSGTANFPYL VTPEQAIQRE VISNGGNVFA  480
VTDNGALSQM ADVASQSSVS LVFVNADSGE GFISVDGNEG DRKNLTLWKN GEAVIDTVVS  540
HCNNTIVVIH SVGPVLIDRW YDNPNVTAII WAGLPGQESG NSLVDVLYGR VNPSAKTPFT  600
WGKTRESYGA PLLTEPNNGN GAPQDDFNEG VFIDYRHFDK RNETPIYEFG HGLSYTTFGY  660
SHLRVQALNS SSSAYVPTSG ETKPAPTYGE IGSAADYLYP EGLKRITKFI YPWLNSTDLE  720
DSSDDPNYGW EDSEYIPEGA RDGSPQPLLK AGGAPGGNPT LYQDLVRVSA TITNTGNVAG  780
YEVPQLYVSL GGPNEPRVVL RKFDRIFLAP GEQKVWTTTL NRRDLANWDV EAQDWVITKY  840
PKKVHVGSSS RKLPLRAPLP RVY                                          863

SEQ ID NO: 23          moltype = AA  length = 253
FEATURE                Location/Qualifiers
source                 1..253
                       mol_type = protein
                       organism = Penicillium sp.
SEQUENCE: 23
MLSSTTRTLA FTGLAGLLSA PLVKAHGFVQ GIVIGDQFYS GYIVNSFPYE SNPPPVIGWA  60
TTATDLGFVD GTGYQGPDII CHRNATPAPL TAPVAAGGTV ELQWTPWPDS HHGPVITYLA  120
PCNGNCSTVD KTTLEFFKID QQGLIDDTSP PGTWASDNLI ANNNSWTVTI PNSVAPGNYV  180
LRHEIIALHS ANNKDGAQNY PQCINIEVTG GGSDAPEGTL GEDLYHDTDP GILVDIYEPI  240
ATYTIPGPPE PTF                                                     253

SEQ ID NO: 24          moltype = AA  length = 532
FEATURE                Location/Qualifiers
source                 1..532
                       mol_type = protein
                       organism = Aspergillus fumigatus
SEQUENCE: 24
MLASTFSYRM YKTALILAAL LGSGQAQQVG TSQAEVHPSM TWQSCTAGGS CTTNNGKVVI  60
DANWRWVHKV GDYTNCYTGN TWDTTICPDD ATCASNCALE GANYESTYGV TASGNSLRLN  120
FVTTSQQKNI GSRLYMMKDD STYEMFKLLN QEFTFDVDVS NLPCGLNGAL YFVAMDADGG  180
MSKYPTNKAG AKYGTGYCDS QCPRDLKFIN GQANVEGWQP SSNDANAGTG NHGSCCAEMD  240
IWEANSISTA FTPHPCDTPG QVMCTGDACG GTYSSDRYGG TCDPDGCDFN SFRQGNKTFY  300
GPGMTVDTKS KFTVVTQFIT DDGTSSGTLK EIKRFYVQNG KVIPNSESTW TGVSGNSITT  360
EYCTAQKSLF QDQNVFEKHG GLEGMGAALA QGMVLVMSLW DDHSANMLWL DSNYPTTASS  420
TTPGVARGTC DISSGVPADV EANHPDAYVV YSNIKVGPIG STFNSGGSNP GGGTTTTTTT  480
QPTTTTTTAG NPGGTGVAQH YGQCGGIGWT GPTTCASPYT CQKLNDYYSQ CL          532

SEQ ID NO: 25          moltype = AA  length = 454
FEATURE                Location/Qualifiers
source                 1..454
                       mol_type = protein
                       organism = Aspergillus fumigatus
SEQUENCE: 25
MKHLASSIAL TLLLPAVQAQ QTVWGQCGGQ GWSGPTSCVA GAACSTLNPY YAQCIPGATA  60
TSTTLTTTTA ATTTSQTTTK PTTTGPTTSA PTVTASGNPF SGYQLYANPY YSSEVHTLAM  120
PSLPSSLQPK ASAVAEVPSF VWLDVAAKVP TMGTYLADIQ AKNKAGANPP IAGIFVVYDL  180
PDRDCAALAS NGEYSIANNG VANYKAYIDA IRAQLVKYSD VHTILVIEPD SLANLVTNLN  240
VAKCANAQSA YLECVDYALK QLNLPNVAMY LDAGHAGWLG WPANLGPAAT LFAKVYTDAG  300
SPAAVRGLAT NVANYNAWSL STCPSYTQGD PNCDEKKYIN AMAPLLKEAG FDAHFIMDTS  360
RNGVQPTKQN AWGDWCNVIG TGFGVRPSTN TGDPLQDAFV WIKPGGESDG TSNSTSPRYD  420
AHCGYSDALQ PAPEAGTWFQ AYFEQLLTNA NPSF                              454

SEQ ID NO: 26          moltype = AA  length = 573
FEATURE                Location/Qualifiers
SIGNAL                 1..17
source                 1..573
                       mol_type = protein
                       organism = Gloeophyllum sepiarium
SEQUENCE: 26
MYRFLVCALG LAASVLAQSV DSYVSSEGPI AKAGVLANIG PNGSKASGAS AGVVVASPST  60
SDPDYWYTWT RDSSLVFKSL IDQYTTGIDS TSSLRTLIDD FVTAEANLQQ VSNPSGTLTT  120
GGLGEPKFNV DETAFTGAWG RPQRDGPALR STALITYGNW LLSNGNTSYV TSNLWPIIQN  180
DLGYVVSYWN QSTYDLWEEV DSSSFFTTAV QHRALREGAA FATAIGQTSQ VSSYTTQADN  240
LLCFLQSYWN PSGGYITANT GGGRSGKDAN TLLASIHTYD PSAGCDAATF QPCSDKALSN  300
LKVYVDSFRS VYSINSGVAS NAAVATGRYP EDSYQGGNPW YLTTFAVAEQ LYDALNVWES  360
QGSLEVTSTS LAFFQQFSSG VTAGTYSSSS STYSTLTSAI KNFADGFVAI NAKYTPSNGG  420
LAEQYSKSDG SPLSAVDLTW SYASALTAFE ARNNTQFAGW GAAGLTVPSS CSGNSGGPTV  480
AVTFNVNAET VWGENIYLTG SVDALENWSA DNALLLSSAN YPTWSITVNL PASTAIEYKY  540
IRKNNGAVTW ESDPNNSITT PASGSTTEND TWR                               573

SEQ ID NO: 27          moltype = AA  length = 576
FEATURE                Location/Qualifiers
SIGNAL                 1..17
source                 1..576
                       mol_type = protein
                       organism = Gloeophyllum trabeum
SEQUENCE: 27
```

-continued

```
MYRFLVCALG LLGTVLAQSV DSYVGSEGPI AKAGVLANIG PNGSKASGAA AGVVVASPSK  60
SDPDYWYTWT RDSSLVFKSL IDQYTTGIDS TSSLRSLIDS FVIAEANIQQ VSNPSGTLTT  120
GGLGEPKFNV DETAFTGAWG RPQRDGPALR ATALITYGNW LLSNGNTTWV TSTLWPIIQN  180
DLNYVVQYWN QTTFDLWEEV NSSSFFTTAV QHRALREGAA FATKIGQTSS VSSYTTQAAN  240
LLCFLQSYWN PTSGYITANT GGGRSGKDAN TLLASIHTYD PSAGCDATTF QPCSDKALSN  300
LKVYVDSFRS VYSINSGIAS NAAVATGRYP EDSYQGGNPW YLTTFAVAEQ LYDALNVWAA  360
QGSLNVTSIS LPFFQQFSSS VTAGTYASSS TTYTTLTSAI KSFADGFVAI NAQYTPSNGG  420
LAEQFSRSNG APVSAVDLTW SYASALTAFE ARNNTQFAGW GAVGLTVPTS CSSNSGGGGG  480
STVAVTFNVN AQTVWGENIY ITGSVDALSN WSPDNALLLS SANYPTWSIT VNLPASTAIQ  540
YKYIRKNNGA VTWESDPNNS ITTPASGSVT ENDTWR                            576

SEQ ID NO: 28          moltype = AA  length = 573
FEATURE                Location/Qualifiers
SIGNAL                 1..18
source                 1..573
                       mol_type = protein
                       organism = Pycnoporus sanguineus
SEQUENCE: 28
MRFTLLASLI GLAVGAFAQS SAVDAYVASE SPIAKQGVLN NIGPNGSKAH GAKAGIVVAS  60
PSTENPDYLY TWTRDSSLVF KLLIDQFTSG DDTSLRGLID DFTSAEAILQ QVSNPSGTVS  120
TGGLGEPKFN IDETAFTGAW GRPQRDGPAL RATSIIRYAN WLLDNGNTTY VSNTLWPVIQ  180
LDLDYVADNW NQSTFDLWEE VDSSSFFTTA VQHRALREGA TFASRIGQSS VVSGYTTQAD  240
NLLCFLQSYW NPSGGYVTAN TGGGRSGKDS NTVLTSIHTF DPAAGCDAAT FQPCSDKALS  300
NLKVYVDAFR SIYTINNGIA SNAAVATGRY PEDSYMGGNP WYLTTSAVAE QLYDALYVWD  360
QLGGLNVTST SLAFFQQFAS GLSTGTYSAS SSTYATLTSA IRSFADGFLA INAKYTPADG  420
GLAEQYSRND GTPLSAVDLT WSYAAALTAF AAREGKTYGS WGAAGLTVPA SCSGGGGATV  480
AVTFNVQATT VFGENIYITG SVAALQNWSP DNALILSAAN YPTWSITVNL PANTVVQYKY  540
IRKFNGQVTW ESDPNNQITT PSGGSFTQND VWR                               573

SEQ ID NO: 29          moltype = AA  length = 413
FEATURE                Location/Qualifiers
source                 1..413
                       mol_type = protein
                       organism = Pyrococcus furiosus
SEQUENCE: 29
AELEGLDESA AQVMATYVWN LGYDGSGITI GIIDTGIDAS HPDLQGKVIG WVDFVNGRSY  60
PYDDHGHGTH VASIAAGTGA ASNGKYKGMA PGAKLAGIKV LGADGSGSIS TIIKGVEWAV  120
DNKDKYGIKV INLSLGSSQS SDGTDALSQA VNAAWDAGLV VVVAAGNSGP NKYTIGSPAA  180
ASKVITVGAV DKYDVITSFS SRGPTADGRL KPEVVAPGNW IIAARASGTS MGQPINDYYT  240
AAPGTSMATP HVAGIAALLL QAHPSWTPDK VKTALIETAD IVKPDEIADI AYGAGRVNAY  300
KAINYDNYAK LVFTGYVANK GSQTHQFVIS GASFVTATLY WDNANSDLDL YLYDPNGNQV  360
DYSYTAYYDF EKVGYYNPTD GTWTIKVVSY SGSANYQVDV VSDGSLSQPG SSP         413
```

PROCESSES FOR PRODUCING FERMENTATION PRODUCTS

CROSS-REFERENCE TO RELATED APPLICATIONS

This application is a continuation of U.S. application Ser. No. 17/229,246 filed Apr. 13, 2021, now U.S. Pat. No. 11,987,831, which is a continuation of U.S. application Ser. No. 16/702,746 filed Dec. 4, 2019, now abandoned, which is a divisional of U.S. application Ser. No. 15/961,269 filed Apr. 24, 2018, now U.S. Pat. No. 10,526,620, which is a divisional of U.S. application Ser. No. 14/648,477 filed May 29, 2015, now U.S. Pat. No. 10,227,613, which is a continuation-in-part under 35 U.S.C. 120 of U.S. patent application Ser. No. 14/388,595 filed on Sep. 26, 2014, now U.S. Pat. No. 9,856,498, as a U.S. National Phase Application under 35 U.S. C. 371 of International Application No. PCT/US2013/034337 filed on Mar. 28, 2013, which claims the benefit under 35 U.S.C. 119 of U.S. Provisional Application No. 61/617,799, filed on Mar. 30, 2012; and, a 35 U.S.C. 371 national application of PCT/US2013/071982 filed Nov. 26, 2013, which claims priority or the benefit under 35 U.S.C. 119 of U.S. provisional application No. 61/731,806 filed Nov. 30, 2012, the contents of which are fully incorporated herein by reference.

FIELD OF THE INVENTION

The present invention relates to processes for producing fermentation products from starch-containing material. The invention also relates to a composition suitable for use in a process of the invention.

REFERENCE TO A SEQUENCE LISTING

This application contains a Sequence Listing in computer readable form. The contents of the electronic sequence listing created on Apr. 15, 2024, named SQ ST26.xml and 48 KB in size, is hereby incorporated by reference in its entirety.

BACKGROUND OF THE INVENTION

Production of fermentation products, such as ethanol, from starch-containing material is well-known in the art. Industrially two different kinds of processes are used today. The most commonly used process, often referred to as a "conventional process", and includes liquefying gelatinized starch at high temperature using typically a bacterial alpha-amylase, followed by simultaneous saccharification and fermentation carried out in the presence of a glucoamylase and a fermentation organism. Another well-known process, often referred to as a "raw starch hydrolysis"-process (RSH process), includes simultaneously saccharifying and fermenting granular starch below the initial gelatization temperature typically in the presence of at least a glucoamylase.

Despite significant improvement of fermentation product production processes over the past decade a significant amount of residual starch material is not converted into the desired fermentation product, such as ethanol. At least some of the unconverted residual starch material, e.g., sugars and dextrins, is in the form of non-fermentable Maillard products.

Therefore, there is still a desire and need for providing processes for producing fermentation products, such as ethanol, from starch-containing material that can provide a higher fermentation product yield, or other advantages, compared to a conventional process.

SUMMARY OF THE INVENTION

The present invention relates to processes of producing fermentation products, such as ethanol, from starch-containing material using a fermenting organism.

In the first aspect the invention relates to processes for producing fermentation products, such as ethanol, from starch-containing material comprising the steps of:

i) liquefying the starch-containing material at a temperature above the initial gelatinization temperature using:
    - an alpha-amylase;
    - optionally a protease having a thermostability value of more than 20% determined as Relative Activity at 80° C./70° C.; and
    - optionally a carbohydrate-source generating enzyme;

ii) saccharifying using a carbohydrate-source generating enzyme;

iii) fermenting using a fermenting organism;

wherein a cellulolytic composition is present or added during fermentation or simultaneous saccharification and fermentation.

Suitable cellulolytic compositions are described below. In a preferred embodiment the cellulolytic composition is derived from *Trichoderma reesei*.

In a preferred embodiment liquefaction is carried out at a temperature between from 70-100° C., such as between 75-95° C., such as between 75-90° C., preferably between 80-90° C., such as 82-88° C., such as around 85° C.

In an embodiment the pH during liquefaction is from 4.5-5.0, such as between 4.5-4.8. In another embodiment liquefaction is carried out at a pH above 5.0-6.5, such as above 5.0-6.0, such as above 5.0-5.5, such as between 5.2-6.2, such as around 5.2, such as around 5.4, such as around 5.6, such as around 5.8.

In a second aspect the invention relates to an enzyme composition comprising:

- an alpha-amylase;
- optionally a protease having a thermostability value of more than 20% determined as Relative Activity at 80° C./70° C.; and
- optionally a pullulanase;
- optionally a carbohydrate-source generating enzyme.

The alpha-amylase present may be any alpha-amylase, preferably a bacterial alpha-amylase, in particular from *Bacillus stearothermophilus*, especially a thermostable variant thereof. Examples of thermostable variants are given below. Preferred examples include alpha-amylases selected from the group of *Bacillus stearothermophilus* alpha-amylase variants:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V;

I181*+G182*+N193F+V59A+E129V+K177L+R179E+Q254S+M284V; and

I181*+G182*+N193F+E129V+K177L+R179E+K220P+N224L+S242Q+Q254S.

The composition of the invention optionally comprises a pullulanase. The pullulanase may be a family GH57 pullulanase, such as a pullulanase which includes an X47 domain as disclosed in WO 2011/087836. More examples are given in the "Pullulanase Present and/or Added During Liquefaction"-section below.

In embodiments of the invention a thermostable protease and/or a carbohydrate-source generating enzyme, in particular a glucoamylases, are optionally present.

Examples of thermostable proteases can be found in the "Protease Present and/or Added During Liquefaction"-section below. In a preferred embodiment the thermostable protease is a variant of the *Thermoascus aurantiacus* protease shown in SEQ ID NO: 3 herein or a protease derived from a strain of *Pyrococcus furiosus*, in particular the one shown in SEQ ID NO: 13 herein, SEQ ID NO: 29 herein or disclosed in U.S. Pat. No. 6,358,726-B1.

Examples of suitable optional carbohydrate-source generating enzymes, preferably thermostable carbohydrate-source generating enzymes, in particular a thermostable glucoamylase, can be found in the "Carbohydrate-Source Generating Enzymes Present and/or Added During Liquefaction"-section below.

In an embodiment the carbohydrate-source generating enzyme, in particular a glucoamylase, is *Penicillium oxalicum* glucoamylase, or a variant thereof.

Other enzyme activities may also be present.

Definitions

Enzymes:

Cellulolytic composition, cellulolytic enzymes or cellulase means a preparation comprising one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, CA, USA).

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptide having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose.

For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, J. Basic Microbiol. 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178).

Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

DETAILED DESCRIPTION OF THE INVENTION

The present invention relates to processes of producing fermentation products, such as ethanol from starch-containing material using a fermenting organism.

In the first aspect the invention relates to processes for producing fermentation products, preferably ethanol, comprising the steps of:

i) liquefying the starch-containing material at a temperature above the initial gelatinization temperature using:
   an alpha-amylase;
   optionally a protease having a thermostability value of more than 20% determined as Relative Activity at 80° C./70° C.; and
   optionally a carbohydrate-source generating enzyme;
ii) saccharifying using a carbohydrate-source generating enzyme;
iii) fermenting using a fermenting organism;

wherein a cellulolytic composition is present or added during fermentation or simultaneous saccharification and fermentation.

Steps ii) and iii) are carried out either sequentially or simultaneously. In a preferred embodiment steps ii) and iii) are carried out simultaneously. The alpha-amylase, optional thermostable protease, optional carbohydrate-source generating enzyme, preferably glucoamylase, and/or, optional a pullulanase, may be added before and/or during liquefaction step i). A composition of the invention may suitably be used in a process of the invention. However, the enzymes may also be added separately. Examples of alpha-amylases can be found in the "Alpha-Amylase Present and/or Added During Liquefaction"-section below. Examples of thermostable proteases can be found in the "Protease Present and/or Added During Liquefaction"-section below. Examples of suitable optional carbohydrate-source generating enzymes, preferably thermostable carbohydrate-source generating enzymes, in particular a thermostable glucoamylase, can be found in the "Carbohydrate-Source Generating Enzymes Present and/or Added During Liquefaction"-section below. A suitable optional pullulanase can be found in the "Pullulanase Present and/or Added During Liquefaction"-section below.

The pH during liquefaction may be between 4-7. In an embodiment the pH during liquefaction is from 4.5-5.0, such as between 4.5-4.8. In another embodiment liquefaction is carried out at a pH above 5.0-6.5, such as above 5.0-6.0, such as above 5.0-5.5, such as between 5.2-6.2, such as around 5.2, such as around 5.4, such as around 5.6, such as around 5.8.

According to the invention the temperature is above the initial gelatinization temperature. The term "initial gelatinization temperature" refers to the lowest temperature at which solubilization of starch, typically by heating, begins. The temperature can vary for different starches.

In an embodiment the temperature during liquefaction step i) is in the range from 70-100° C., such as between 75-95° C., such as between 75-90° C., preferably between 80-90° C., such as between 82-88° C., such as around 85° C.

In an embodiment, the process of the invention further comprises, prior to the step i), the steps of:

a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry and wet milling are well known in the art of starch processing. According to the present invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material.

The slurry may be heated to above the initial gelatinization temperature, preferably to between 80-90° C., between pH 4-7, preferably between 4.5-5.0 or 5.0 and 6.0, for 30 minutes to 5 hours, such as around 2 hours.

The alpha-amylase, optional thermostable protease, optional carbohydrate-source generating enzyme, in particular thermostable glucoamylase, and/or optional pullulanase may initially be added to the aqueous slurry to initiate liquefaction (thinning). In an embodiment only a portion of the enzymes is added to the aqueous slurry, while the rest of the enzymes are added during liquefaction step i).

Liquefaction step i) is according to the invention carried out for 0.5-5 hours, such as 1-3 hours, such as typically around 2 hours.

The aqueous slurry may in an embodiment be jet-cooked to further gelatinize the slurry before being subjected to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

Saccharification and Fermentation

One or more carbohydrate-source generating enzymes, in particular glucoamylase, may be present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase. The carbohydrate-source generating enzyme added during saccharification step ii) and/or fermentation step iii) is typically different from the optional carbohydrate-source generating enzyme, in particular thermostable glucoamylase, optionally added during liquefaction step i). In a preferred embodiment the carbohydrate-source generating enzymes, in particular glucoamylase, is added together with a fungal alpha-amylase.

Examples of carbohydrate-source generating enzymes, including glucoamylases, can be found in the "Carbohydrate-Source Generating Enzyme Present and/or Added During Saccharification and/or Fermentation"-section below.

When doing sequential saccharification and fermentation, saccharification step ii) may be carried out at conditions well-known in the art. For instance, the saccharification step ii) may last up to from about 24 to about 72 hours. In an embodiment pre-saccharification is done. Pre-saccharification is typically done for 40-90 minutes at a temperature between 30-65° C., typically about 60° C. Pre-saccharification is in an embodiment followed by saccharification during fermentation in simultaneous saccharification and fermentation ("SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. However, it is also contemplated to add the fermenting organism and enzyme(s) separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" refers to the environment in which fermentation is carried out. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae.*

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5\times10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention an alpha-amylase is present and/or added during liquefaction together with an optional thermostable protease, optional carbohydrate-source generating enzyme, in particular a thermostable glucoamylase, and/or optional pullulanase.

The alpha-amylase added during liquefaction step i) may be any alpha-amylase. Preferred are bacterial alpha-amylases, which typically are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 1 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated so it has around 491 amino acids (compared to SEQ ID NO: 3 in WO 99/19467.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, 1181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467 or SEQ ID NO: 1 herein.

In an embodiment the variant is a S242A, E or Q variant, preferably a S242Q variant, of the *Bacillus stearothermophilus* alpha-amylase (using SEQ ID NO: 1 herein for numbering).

In an embodiment the variant is a position E188 variant, preferably E188P variant of the *Bacillus stearothermophilus* alpha-amylase (using SEQ ID NO: 1 herein for numbering).

The bacterial alpha-amylase may in an embodiment be a truncated *Bacillus licheniformis* alpha-amylase. Especially the truncation is so that the *Bacillus stearothermophilus* alpha-amylase shown in SEQ ID NO: 3 in WO 99/19467 or SEQ ID NO: 1 herein, is around 491 amino acids long, such as from 480 to 495 amino acids long.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions: G48A+T491+G107A+H156Y+A181T+N190F+1201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase may be a thermostable alpha-amylase, such as a thermostable bacterial alpha-amylase, preferably from *Bacillus stearothermophilus*. In an embodiment the alpha-amylase used according to the invention has a T½ (min) at pH 4.5, 85° C., 0.12 mM $CaCl_2$) of at least 10.

In an embodiment the thermostable alpha-amylase has a T½ (min) at pH 4.5, 85° ° C., 0.12 mM $CaCl_2$), of at least 15.

In an embodiment the thermostable alpha-amylase has a T½ (min) at pH 4.5, 85° C., 0.12 mM $CaCl_2$), of as at least 20.

In an embodiment the thermostable alpha-amylase has a T½ (min) at pH 4.5, 85° C., 0.12 mM $CaCl_2$), of as at least 25.

In an embodiment the thermostable alpha-amylase has a T½ (min) at pH 4.5, 85° C., 0.12 mM $CaCl_2$), of as at least 30.

In an embodiment the thermostable alpha-amylase has a T½ (min) at pH 4.5, 85° C., 0.12 mM $CaCl_2$), of as at least 40.

In an embodiment the thermostable alpha-amylase has a T½ (min) at pH 4.5, 85° C., 0.12 mM $CaCl_2$), of at least 50.

In an embodiment the thermostable alpha-amylase has a T½ (min) at pH 4.5, 85° C., 0.12 mM $CaCl_2$), of at least 60.

In an embodiment the thermostable alpha-amylase has a T½ (min) at pH 4.5, 85° C., 0.12 mM $CaCl_2$), between 10-70.

In an embodiment the thermostable alpha-amylase has a T½ (min) at pH 4.5, 85° C., 0.12 mM $CaCl_2$), between 15-70.

In an embodiment the thermostable alpha-amylase has a T½ (min) at pH 4.5, 85° C., 0.12 mM $CaCl_2$), between 20-70.

In an embodiment the thermostable alpha-amylase has a T½ (min) at pH 4.5, 85° C., 0.12 mM $CaCl_2$), between 25-70.

In an embodiment the thermostable alpha-amylase has a T½ (min) at pH 4.5, 85° C., 0.12 mM $CaCl_2$), between 30-70.

In an embodiment the thermostable alpha-amylase has a T½ (min) at pH 4.5, 85° C., 0.12 mM $CaCl_2$), between 40-70.

In an embodiment the thermostable alpha-amylase has a T½ (min) at pH 4.5, 85° C., 0.12 mM $CaCl_2$), between 50-70.

In an embodiment the thermostable alpha-amylase has a T½ (min) at pH 4.5, 85° C., 0.12 mM $CaCl_2$), between 60-70.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 1 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optional substitution N193F, further comprising mutations selected from below list:

| |
|---|
| V59A + Q89R + G112D + E129V + K177L + R179E + K220P + N224L + Q254S; |
| V59A + Q89R + E129V + K177L + R179E + H208Y + K220P + N224L + Q254S; |
| V59A + Q89R + E129V + K177L + R179E + K220P + N224L + Q254S + D269E + D281N; |
| V59A + Q89R + E129V + K177L + R179E + K220P + N224L + Q254S + I270L; |
| V59A + Q89R + E129V + K177L + R179E + K220P + N224L + Q254S + H274K; |
| V59A + Q89R + E129V + K177L + R179E + K220P + N224L + Q254S + Y276F; |
| V59A + E129V + R157Y + K177L + R179E + K220P + N224L + S242Q + Q254S; |
| V59A + E129V + K177L + R179E + H208Y + K220P + N224L + S242Q + Q254S; |
| V59A + E129V + K177L + R179E + K220P + N224L + S242Q + Q254S; |
| V59A + E129V + K177L + R179E + K220P + N224L + S242Q + Q254S + H274K; |
| V59A + E129V + K177L + R179E + K220P + N224L + S242Q + Q254S + Y276F; |
| V59A + E129V + K177L + R179E + K220P + N224L + S242Q + Q254S + D281N; |
| V59A + E129V + K177L + R179E + K220P + N224L + S242Q + Q254S + M284T; |
| V59A + E129V + K177L + R179E + K220P + N224L + S242Q + Q254S + G416V; |
| V59A + E129V + K177L + R179E + K220P + N224L + Q254S; |
| V59A + E129V + K177L + R179E + K220P + N224L + Q254S + M284T; |
| A91L + M96I + E129V + K177L + R179E + K220P + N224L + S242Q + Q254S; |
| E129V + K177L + R179E; |
| E129V + K177L + R179E + K220P + N224L + S242Q + Q254S; |
| E129V + K177L + R179E + K220P + N224L + S242Q + Q254S + Y276F + L427M; |
| E129V + K177L + R179E + K220P + N224L + S242Q + Q254S + M284T; |
| E129V + K177L + R179E + K220P + N224L + S242Q + Q254S + N376* + I377*; |
| E129V + K177L + R179E + K220P + N224L + Q254S; |
| E129V + K177L + R179E + K220P + N224L + Q254S + M284T; |
| E129V + K177L + R179E + S242Q; |
| E129V + K177L + R179V + K220P + N224L + S242Q + Q254S; |
| K220P + N224L + S242Q + Q254S; |
| M284V; |
| V59A + Q89R + E129V + K177L + R179E + Q254S + M284V. |
| V59A + E129V + K177L + R179E + Q254S + M284V; |

In a preferred embodiment the alpha-amylase is selected from the group of *Bacillus stearothermophilus* alpha-amylase variants:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V;

I181*+G182*+N193F+V59A+E129V+K177L+R179E+Q254S+M284V; and

I181*+G182*+N193F+E129V+K177L+R179E+K220P+N224L+S242Q+Q254S (using SEQ ID NO: 1 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 1 herein, or variants thereof, are truncated in the C-terminal and are typically around 491 amino acids long, such as from 480-495 amino acids long.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 1 herein.

Protease Present and/or Added During Liquefaction

According to the invention a thermostable protease is optionally present and/or added during liquefaction together with an alpha-amylase, and optionally a carbohydrate-source generating enzyme, in particular a thermostable glucoamylase, and/or optionally a pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

In one embodiment the protease is of fungal origin.

The protease may be a variant of, e.g., a wild-type protease as long as the protease has the thermostability properties defined herein. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease)

In an embodiment the protease is one shown as SEQ ID NO: 1 in U.S. Pat. No. 6,358,726-B1 (Takara Shuzo Company), SEQ ID NO: 13 herein or SEQ ID NO: 29 herein.

In another embodiment the thermostable protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found to have a thermostability of 110% (80° C./70° C.) and 103% (90° C./70° C.) at pH 4.5 determined as described in Example 2 herein.

In one embodiment a thermostable protease used in a process of the invention has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C. In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2.

In an embodiment the protease may have a themostability for above 90, such as above 100 at 85° C. as determined using the Zein-BCA assay as disclosed in Example 3.

In an embodiment the protease has a themostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

Carbohydrate-Source Generating Enzyme Present and/or Added During Liquefaction

According to the invention a carbohydrate-source generating enzyme, in particular a glucoamylase, preferably a thermostable glucoamylase, may optionally be present and/or added during liquefaction together with an alpha-amylase and an optional thermostable protease. As mentioned above, a pullulanase may also be optionally be present and/or added during liquefaction step i).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In an embodiment the carbohydrate-source generating enzyme, preferably a thermostable glucoamylase, has a Relative Activity heat stability at 85° C. of at least 20%, at least 30%, preferably at least 35% determined as described in Example 4 (heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in PCT/CN10/071753 published as WO 2011/127802 (which is hereby incorporated by reference) and shown in SEQ ID NO: 9 or 14 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 9 and 14 herein, having a K79V substitution (using the mature sequence shown in SEQ ID NO: 14 for numbering). The K79V glucoamylase variant has reduced sensitivity to protease degradation relative to the parent as disclosed in U.S. application No. 61/531,189 or PCT/US12/053779 (which are hereby incorporated by reference).

In an embodiment the carbohydrate-source generating enzyme, in particular thermostable glucoamylase, is derived from *Penicillium oxalicum.*

In an embodiment the thermostable glucoamylase is a variant of the *Penicillium oxalicum* glucoamylase disclosed as SEQ ID NO: 2 in WO 2011/127802 and shown in SEQ ID NO: 9 and 14 herein. In a preferred embodiment the *Penicillium oxalicum* glucoamylase is the one disclosed as SEQ ID NO: 2 in WO 2011/127802 and shown in SEQ ID NO: 9 and 14 herein having Val (V) in position 79 (using SEQ ID NO: 14 for numbering).

Contemplated *Penicillium oxalicum* glucoamylase variants are disclosed in co-pending PCT application #PCT/EP12/070127 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 14 for numbering), corresponding to the PE001 variant, and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+1172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+1172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V791+Q327F+E501V+Y504T; or

P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the *Penicillium oxalicum* glucoamylase variant has a K79V substitution (using SEQ ID NO: 14 for numbering), corresponding to the PE001 variant, and further comprises one of the following mutations:

P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The carbohydrate-source generating enzyme, in particular, may be added in amounts from 0.1-100 micrograms EP/g, such as 0.5-50 micrograms EP/g, such as 1-25 micrograms EP/g, such as 2-12 micrograms EP/g DS.

Pullulanase Present and/or Added During Liquefaction

Optionally a pullulanase may be present and/or added during liquefaction step i) together with an alpha-amylase and optionally a thermostable protease and/or carbohydrate-source generating enzyme. As mentioned above a carbohydrate-source generating enzyme, preferably a thermostable glucoamylase, may also be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO92/02614.

In an embodiment the pullulanase is a family GH57 pullulanase. In an embodiment the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12 herein). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference) and disclosed in SEQ ID NO: 12 herein.

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (DuPont-Genencor, USA), and AMANO 8 (Amano, Japan).

Carbohydrate-Source Generating Enzyme Present and/or Added During Saccharification and/or Fermentation According to the invention a carbohydrate-source generating enzyme, preferably a glucoamylase, may be present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii,*

Glucoamylase

According to the invention the glucoamylase present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability:

G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus* as described in WO 2011/066576 (SEQ ID NOs 2, 4 or 6), such as SEQ ID NO: 28 herein, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 26 herein. In a preferred embodiment the glucoamylase is SEQ ID NO: 27 herein. In an embodiment the glucoamylase is derived from a strain of the genus *Nigrofomes*, in particular a strain of *Nigrofomes* sp. disclosed in WO 2012/064351 (SEQ ID NO: 2) (all references hereby incorporated by reference). Contemplated are also glucoamylases which exhibit a high identity to any of the above mentioned glucoamylases, i.e., at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 26, 27, 28 or 29 herein, preferably SEQ ID NO: 26 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 7 and *Trametes cingulata* glucoamylase disclosed in WO 06/069289.

In an embodiment the glucoamylase is a blend comprising *Talaromyces emersonii* glucoamylase disclosed in WO 99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290.

In an embodiment the glucoamylase is a blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290.

In an embodiment the glucoamylase is a blend comprising *Gloeophyllum sepiarium* glucoamylase shown as SEQ ID NO: 2 in WO 2011/068803 and *Rhizomucor pusillus* with an *Aspergillus niger* glucoamylase linker and starch-binding domain (SBD), disclosed SEQ ID NO: 3 in WO 2013/006756 with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*.

In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290.

In an embodiment the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering). In a preferred embodiment the glucoamylase blend comprises *Gloeophyllum sepiarium* glucoamylase (e.g., SEQ ID NO: 2 in WO 2011/068803) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 and *Rhizomucor pusillus* with an *Aspergillus niger* glucoamylase linker and starch-binding domain (SBD), disclosed SEQ ID NO: 3 in WO 2013/006756 with the following substitutions: G128D+D143N Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE and AMG™ E (from Novozymes A/S); OPTIDEX™ 300, GC480, GC417 (from DuPont-Genencor); AMIGASE™ and AMIGASET PLUS (from DSM); G-ZYME™ G900, G-ZYMET and G990 ZR (from DuPont-Genencor).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Cellulolytic Composition Present and/or Added During Saccharification and/or Fermentation According to the invention a cellulolytic composition is present during fermentation or simultaneous saccharification and fermentation (SSF).

The cellulolytic composition may be any cellulolytic composition, comprising a beta-glucosidase, a cellobiohydrolase and an endoglucanase.

Examples of suitable cellulolytic composition can be found in WO 2008/151079 and co-pending patent application PCT/US12/052163 published as WO 2013/028928 which are incorporated by reference.

In preferred embodiments the cellulolytic composition is derived from a strain of *Trichoderma, Humicola*, or *Chrysosporium.*

In an embodiment the cellulolytic composition is derived from a strain of *Trichoderma reesei, Humicola insolens* and/or *Chrysosporium lucknowense.*

In an embodiment the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in WO 2005/047499 or SEQ ID NO: 22 herein or an *Aspergillus fumigatus* beta-glucosidase variant disclosed in WO 2012/044915 (Novozymes), such as one with the following substitutions F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei.*

In an embodiment the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 23 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 2 in WO 2011/057140 or SEQ ID NO: 24 herein, or a strain of the genus *Trichoderma*, such as a strain of *Trichoderma reesei.*

In an embodiment the cellulolytic composition comprises a cellobiohydrolase II (CBH II, such as one derived from a strain of the genus *Aspergillus*, such as a strain of *Aspergillus fumigatus* or SEQ ID NO: 25 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris.*

In an embodiment the cellulolytic composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 22 herein.

In an embodiment the cellulolytic composition is a *Trichoderma reesei* cellulolytic enzyme composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or SEQ ID NO: 22 herein or a variant thereof with the following substitutions F100D, S283G, N456E, F512Y.

In a preferred embodiment the cellulolytic composition comprising one or more of the following components:

(i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

In an preferred embodiment the cellulolytic composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 23 herein), *Aspergillus fumigatus* beta-glucosidase (SEQ ID NO: 2 in WO 2005/047499 SEQ ID NO: 22 herein) variant F100D, S283G, N456E, F512Y) disclosed in WO 2012/044915; *Aspergillus fumigatus* Cel7A CBH1 disclosed as SEQ ID NO: 6 in WO2011/057140 (SEQ ID NO: 24 herein) and *Aspergillus fumigatus* CBH II disclosed as SEQ ID NO: 18 in WO 2011/057140 (SEQ ID NO: 25 herein).

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

EXAMPLES OF PREFERRED PROCESSES OF THE INVENTION

In a preferred embodiment the process of the invention relates to a process for producing fermentation products from starch-containing material comprising the steps of:

i) liquefying the starch-containing material at a temperature above the initial gelatinization temperature using:
an alpha-amylase derived from *Bacillus stearothermophilus;*
optionally a protease having a thermostability value of more than 20% determined as Relative Activity at 80° C./70° C., preferably derived from *Pyrococcus furiosus* and/or *Thermoascus aurantiacus*; and
optionally a *Penicillium oxalicum* glucoamylase;
ii) saccharifying using a glucoamylase enzyme;
iii) fermenting using a fermenting organism;
wherein a cellulolytic composition is present and/or added during fermentation or simultaneous saccharification and fermentation.

In another preferred embodiment the process of the invention relates to a process for producing fermentation products from starch-containing material comprising the steps of:
i) liquefying the starch-containing material at a temperature above the initial gelatinization temperature using:
an alpha-amylase, preferably derived from *Bacillus stearothermophilus*, having a T½ (min) at pH 4.5, 85° C., 0.12 mM $CaCl_2$) of at least 10;
optionally a protease, preferably derived from *Pyrococcus furiosus* and/or *Thermoascus aurantiacus*, having a thermostability value of more than 20% determined as Relative Activity at 80° C./70° C.;
optionally a *Penicillium oxalicum* glucoamylase;
ii) saccharifying using a glucoamylase enzyme;
iii) fermenting using a fermenting organism;
wherein a cellulolytic composition is present and/or added during fermentation or simultaneous saccharification and fermentation.

In another preferred embodiment the process of the invention relates to a process for producing fermentation products from starch-containing material comprising the steps of:
i) liquefying the starch-containing material at a temperature between 80-90° C.:
an alpha-amylase, preferably derived from *Bacillus stearothermophilus*, having a T½ (min) at pH 4.5, 85° C., 0.12 mM $CaCl_2$) of at least 10;
optionally a protease, preferably derived from *Pyrococcus furiosus* and/or *Thermoascus aurantiacus*, having a thermostability value of more than 20% determined as Relative Activity at 80° C./70° C.; and
optionally a *Penicillium oxalicum* glucoamylase
ii) saccharifying using a glucoamylase enzyme;
iii) fermenting using a fermenting organism;
wherein a cellulolytic composition is present and/or added during fermentation or simultaneous saccharification and fermentation.

In another preferred embodiment the process of the invention relates to a process for producing fermentation products from starch-containing material comprising the steps of:
i) liquefying the starch-containing material at a temperature above the initial gelatinization temperature using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+Q254S+M284V;
V59A+E129V+K177L+R179E+Q254S+M284V;
V59A+Q89R+E129V+K177L+R179E+H208Y+K220P+N224L+Q254S;
E129V+K177L+R179E+K220P+N224L+S242Q+Q254S (using SEQ ID NO: 1 herein for numbering).
optionally a protease, preferably derived from *Pyrococcus furiosus* and/or *Thermoascus aurantiacus*, having a thermostability value of more than 20% determined as Relative Activity at 80° C./70° C.; and
optionally a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase enzyme;
iii) fermenting using a fermenting organism;
wherein a cellulolytic composition is present and/or added during fermentation or simultaneous saccharification and fermentation.

In another preferred embodiment the process of the invention relates to a process for producing fermentation products from starch-containing material comprising the steps of:
i) liquefying the starch-containing material at a temperature between 80-90° C. using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+Q254S+M284V;
V59A+E129V+K177L+R179E+Q254S+M284V;
V59A+Q89R+E129V+K177L+R179E+H208Y+K220P+N224L+Q254S;
E129V+K177L+R179E+K220P+N224L+S242Q+Q254S (using SEQ ID NO: 1 herein for numbering).
optionally a protease, preferably derived from *Pyrococcus furiosus* and/or *Thermoascus aurantiacus* having a thermostability value of more than 20% determined as Relative Activity at 80° C./70° C.;
optionally a pullulanase
optionally a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase enzyme;
iii) fermenting using a fermenting organism;
wherein a cellulolytic composition is present and/or added during fermentation or simultaneous saccharification and fermentation.

In another preferred embodiment the process of the invention relates to a process for producing fermentation products from starch-containing material comprising the steps of:
i) liquefying the starch-containing material at a temperature above the initial gelatinization temperature using:

an alpha-amylase derived from *Bacillus stearothermophilus;* optionally a protease, preferably derived from *Pyrococcus furiosus* or *Thermoascus aurantiacus*, having a thermostability value of more than 20% determined as Relative Activity at 80° C./70° C.; and optionally a pullulanase;

optionally a *Penicillium oxalicum* glucoamylase;

ii) saccharifying using a glucoamylase enzyme;

iii) fermenting using a fermenting organism;

wherein a cellulolytic composition is present and/or added during fermentation or simultaneous saccharification and fermentation.

In another preferred embodiment the process of the invention relates to a process for producing fermentation products from starch-containing material comprising the steps of:

i) liquefying the starch-containing material at a temperature above the initial gelatinization temperature using:

an alpha-amylase, preferably derived from *Bacillus stearothermophilus*, having a T½ (min) at pH 4.5, 85° C., 0.12 mM $CaCl_2$) of at least 10;

optionally a protease, preferably derived from *Pyrococcus furiosus* or *Thermoascus aurantiacus*, having a thermostability value of more than 20% determined as Relative Activity at 80° C./70° C.;

optionally a pullulanase;

optionally a *Penicillium oxalicum* glucoamylase;

ii) saccharifying using a glucoamylase enzyme;

iii) fermenting using a fermenting organism;

wherein a cellulolytic composition is present and/or added during fermentation or simultaneous saccharification and fermentation.

In another preferred embodiment the process of the invention relates to a process for producing fermentation products from starch-containing material comprising the steps of:

i) liquefying the starch-containing material at a temperature between 80-90° C.:

an alpha-amylase, preferably derived from *Bacillus stearothermophilus*, having a T½ (min) at pH 4.5, 85° C., 0.12 mM CaCl2 of at least 10;

optionally a protease, preferably derived from *Pyrococcus furiosus* or *Thermoascus aurantiacus*, having a thermostability value of more than 20% determined as Relative Activity at 80° C./70° C.;

optionally a pullulanase;

optionally a *Penicillium oxalicum* glucoamylase;

ii) saccharifying using a glucoamylase enzyme;

iii) fermenting using a fermenting organism;

wherein a cellulolytic composition is present and/or added during fermentation or simultaneous saccharification and fermentation.

In another preferred embodiment the process of the invention relates to a process for producing fermentation products from starch-containing material comprising the steps of:

i) liquefying the starch-containing material at a temperature above the initial gelatinization temperature using:

an alpha-amylase derived from *Bacillus stearothermophilus* having a double deletion I181+G182 and optional substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering);

optionally a protease, derived from *Pyrococcus furiosus* and/or *Thermoascus aurantiacus*, having a thermostability value of more than 20% determined as Relative Activity at 80° C./70° C.; and optionally a pullulanase;

optionally a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition is present and/or added during fermentation or simultaneous saccharification and fermentation.

In another preferred embodiment the process of the invention relates to a process for producing fermentation products from starch-containing material comprising the steps of:

i) liquefying the starch-containing material at a temperature between 80-90° C. using:

an alpha-amylase derived from *Bacillus stearothermophilus* having a double deletion I181+G182 and optional substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering).

optionally a protease, derived from *Pyrococcus furiosus* and/or *Thermoascus aurantiacus*, having a thermostability value of more than 20% determined as Relative Activity at 80° C./70° C.;

and optionally optionally a pullulanase;

optionally a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition is present and/or added during fermentation or simultaneous saccharification and fermentation.

In an embodiment the process of the invention comprises the steps of:

i) liquefying the starch-containing material at a temperature between 80-90° C. at a pH between 5.0 and 6.5 using:

an alpha-amylase derived from *Bacillus stearothermophilus* having a double deletion I181+G182+N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V

E129V+K177L+R179E+K220P+N224L+S242Q+Q254S (using SEQ ID NO: 1 herein for numbering).

a protease derived from *Pyrococcus furiosus*, preferably the one shown in SEQ ID NO: 13 herein or 29 herein;

a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition, such as a *Trichoderma reesei* cellulolytic composition, is present and/or added during fermentation or simultaneous saccharification and fermentation, in particular a *Trichoderma reesei* cellulolytic composition comprising one or more polypeptides selected from the group consisting of:

GH61 polypeptide having cellulolytic enhancing activity, beta-glucosidase;

Cellobiohydrolase I;

Cellobiohydrolase II;

or a mixture of two, three, or four thereof.

In an embodiment the invention relates to processes, comprising the steps of:

i) liquefying the starch-containing material at a temperature between 80-90° ° C. at a pH between 5.0 and 6.5 using:

an alpha-amylase derived from *Bacillus stearothermophilus* having a double deletion I181+G182+N193F+V59A+Q89R+E129V+K177L+R179E+Q254S+M284V (using SEQ ID NO: 1 herein for numbering).

a protease derived from *Pyrococcus furiosus*, preferably the one shown in SEQ ID NO: 13 herein or SEQ ID NO: 29 herein;

a *Penicillium oxalicum* glucoamylase shown in SEQ ID NO: 14 having substitutions selected from the group of:

K79V+P11F+T65A+Q327F

K79V+P2N+P4F+P11F+T65A+Q327F (using SEQ ID NO: 14 for numbering).

ii) saccharifying using a glucoamylase enzyme selected from the group of *Talaromyces emersonii* glucoamylase or *Gloeophyllum serpiarium* glucoamylase;

iii) fermenting using a *Saccharomyces cerevisiae* yeast wherein a *Trichoderma reesei* cellulolytic composition is present and/or added during fermentation or simultaneous saccharification and fermentation.

In an embodiment the pullulanase present and/or added during liquefaction step i) is a family GH57 pullulanase, wherein the pullulanase preferably includes an X47 domain as disclosed in WO 2011/087836.

In another embodiment the pullulanase is derived from a strain from the genus *Thermococcus*, including *Thermococcus litoralis* and *Thermococcus hydrothermalis*, or a hybrid thereof.

In an embodiment the pullulanase is truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

In an embodiment the *Bacillus stearothermophilus* alpha-amylase (SEQ ID NO: 1 herein) is the mature alpha-amylase or corresponding mature alpha-amylases having at least 80% identity, at least 90% identity, at least 95% identity at least 96% identity at least 97% identity at least 99% identity to the SEQ ID NO: 1.

In an embodiment the *Pyrococcus furiosus* protease (SEQ ID NO: 13 herein or SEQ ID NO: 29 herein) and/or *Thermoascus aurantiacus* protease (SEQ ID NO: 3) are the mature proteases or corresponding mature proteases having at least 80% identity, at least 90% identity, at least 95% identity at least 96% identity at least 97% identity at least 99% identity to the SEQ ID NO: 13 or SEQ ID NO: 29 herein, or SEQ ID NO: 3, respectively.

In an embodiment the *Penicillium oxalicum* glucoamylase (SEQ ID NO: 14 herein) is the mature glucoamylase or corresponding mature glucoamylase having at least 80% identity, at least 90% identity, at least 95% identity at least 96% identity at least 97% identity at least 99% identity to the SEQ ID NO: 14 herein.

A Composition Comprising Alpha-Amylase and Protease

A composition of the invention comprises an alpha-amylase and a thermostable protease. The composition may also further comprise a thermostable carbohydrate-source generating enzyme and/or optionally a pullulanase too.

Therefore, in this aspect the invention relates to composition comprising:

i) an alpha-amylase;

ii) a protease has a thermostability value of more than 20% determined as Relative Activity at 80° C./70° C.; and optionally iii) a carbohydrate-source generating enzyme.

Alpha-amylase: The alpha-amylase may be any alpha-amylase, such as bacterial alpha-amylases, such as alpha-amylases derived from the genus *Bacillus*, such as *Bacillus stearothermophilus*.

The alpha-amylase may be a thermostable alpha-amylase. The thermostable alpha-amylase may have a T½ (min) at pH 4.5, 85° C., 0.12 mM $CaCl_2$)) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus stearothermophilus* alpha-amylase variants, in particular truncated to be 491 amino acids long, such as from 480 to 495 amino acids long, with mutations selected from the group of:

I181*+G182*+N193F+E129V+K177L+R179E;

I181*+G182*+N193F+V59A+Q89R+E129V+K177L+R179E+H208Y+K220P+N224L+Q254S;

I181*+G182*+N193F+V59A+Q89R+E129V+K177L+R179E+Q254S+M284V;

I181*+G182*+N193F+V59A+E129V+K177L+R179E+Q254S+M284V; and

I181*+G182*+N193F+E129V+K177L+R179E+K220P+N224L+S242Q+Q254S (using SEQ ID NO: 1 herein for numbering).

It should be understood that these alpha-amylases are only specific examples. Any alpha-amylase disclosed above in the "Alpha-Amylase Present and/or Added During Liquefaction"—section above may be used as the alpha-amylase component in a composition of the invention.

Protease: A composition of the invention comprises a thermostable protease.

There is no limitation on the origin of the protease component as long as it fulfills the thermostability properties defined herein.

In a preferred embodiment the protease is a variant of the *Thermoascus aurantiacus* protease mentioned above having a thermostability value of more than 20% determined as Relative Activity at 80° C./70° C. determined as described in Example 2.

In a specific preferred embodiment the protease is a variant of the metallo protease derived from *Thermoascus aurantiacus* disclosed as the mature part of SEQ ID NO. 2 disclosed in WO 2003/048353 or the mature part of SEQ ID NO: 1 in WO 2010/008841 or SEQ ID NO: 3 herein with mutations selected from the group of:

D79L+S87P+A112P+D142L;

D79L+S87P+D142L; and

A27K+D79L+Y82F+S87G+D104P+A112P+A126V+D142L.

In another preferred embodiment the protease is derived from a strain of *Pyrococcus furiosus*, such as the one shown in SEQ ID NO: 1 in U.S. Pat. No. 6,358,726, SEQ ID NO: 13 herein or SEQ ID NO: 29 herein.

It should be understood that these proteases are only examples. Any protease disclosed above in the "Protease Present and/or Added During Liquefaction" section above may be used as the protease component in a composition of the invention.

Carbohydrate-source generating enzymes: A composition of the invention may further comprise a carbohydrate-source generating enzyme, in particular a glucoamylase, which has a heat stability at 85° C., pH 5.3, of at least 30%, preferably at least 35%.

Said carbohydrate-source generating enzyme may be a thermostable glucoamylase having a Relative Activity heat stability at 85° C. of at least 20%, at least 30%, preferably at least 35% determined as described in Example 4 (Heat stability).

In an embodiment the carbohydrate-source generating enzyme is a glucoamylase having a relative activity pH optimum at pH 5.0 of at least 90%, preferably at least 95%, preferably at least 97%, such as 100% determined as described in Example 4 (pH optimum).

In an embodiment the carbohydrate-source generating enzyme is a glucoamylase having a pH stability at pH 5.0 of at least at least 80%, at least 85%, at least 90% determined as described in Example 4 (pH stability).

In a preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in PCT/CN10/071753 published as WO 2011/127802 (which is hereby incorporated by reference), or a variant thereof, and shown in SEQ ID NO: 9 or 14 herein.

In an embodiment the glucoamylase, or a variant thereof, may have at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 9 or 14 herein.

In a specific and preferred embodiment the carbohydrate-source generating enzyme is a variant of the *Penicillium oxalicum* glucoamylase disclosed as SEQ ID NO: 2 in WO 2011/127802 and shown in SEQ ID NO: 9 and 14 herein, having a K79V substitution (using the mature sequence shown in SEQ ID NO: 14 for numbering). The K79V glucoamylase variant has reduced sensitivity to protease degradation relative to the parent as disclosed in U.S. application No. 61/531,189 published as WO 2013/036526 (which is hereby incorporated by reference).

Examples of suitable thermostable *Penicillium oxalicum* glucoamylase variants are listed above and in Examples 15 and 16 below or Examples 10 and 11 in WO 2013/053801 (hereby incorporated by reference).

In an embodiment the carbohydrate-source generating enzyme has pullulanase side activity.

It should be understood that these carbohydrate-source generating enzymes, in particular glucoamylases, are only examples. Any carbohydrate-source generating enzyme disclosed above in the "Carbohydrate-source generating enzyme Present and/or Added During Liquefaction" section above may be used as component in a composition of the invention.

Pullulanase: A composition of the invention may further comprise a pullulanase. In an embodiment the pullulanase is a family GH57 pullulanase In a preferred embodiment the pullulanase includes an X47 domain as disclosed in U.S. 61/289,040 published as WO 2011/087836 (which are hereby incorporated by reference).

Specifically the pullulanase may be derived from a strain from the genus *Thermococcus*, including *Thermococcus litoralis* and *Thermococcus hydrothermalis* or a hybrid thereof.

The pullulanase may be *Thermococcus hydrothermalis* pullulanase truncated at site X4 or a *Thermococcus hydrothermalis/T. litoralis* hybrid enzyme with truncation site X4 as disclosed in U.S. 61/289,040 published as WO 2011/087836.

In another embodiment the pullulanase is one comprising an X46 domain disclosed in WO 2011/076123 (Novozymes).

It should be understood that these pullulanases are only specific examples. Any pullulanase disclosed above in the "Pullulanase Present and/or Added During Liquefaction" section above may be used as the optional pullulanase component in a composition of the invention.

Preferred Compositions of the Invention

In a preferred embodiment the composition of the invention comprising an alpha-amylase derived from *Bacillus stearothermophilus;* optionally a protease, preferably derived from *Pyrococcus furiosus* and/or *Thermoascus aurantiacus*, having a thermostability value of more than 20% determined as Relative Activity at 80° C./70° C.; and optionally optionally a glucoamylase derived from *Penicillium oxalicum.*

The glucoamylase may optionally be substituted or combined with a pullulanase preferably derived from *Thermococcus litoralis* or *Thermococcus hydrothermalis.*

In a preferred embodiment the composition comprises an alpha-amylase, preferably derived from *Bacillus stearothermophilus*, having a T½ (min) at pH 4.5, 85° C., 0.12 mM $CaCl_2$) of at least 10;

optionally a protease, preferably derived from *Pyrococcus furiosus* or *Thermoascus aurantiacus*, having a thermostability value of more than 20% determined as Relative Activity at 80° C./70° C.;

optionally a glucoamylase derived from *Penicillium oxalicum.*

In a preferred embodiment the composition comprises an alpha-amylase derived from *Bacillus stearothermophilus* having a double deletion I181+G182 and substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering).

optionally a protease having a thermostability value of more than 20% determined as Relative Activity at 80° C./70° C. derived from *Pyrococcus furiosus* and/or *Thermoascus aurantiacus*; and optionally a *Penicillium oxalicum* glucoamylase in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering). In an embodiment the composition comprises:

an alpha-amylase derived from *Bacillus stearothermophilus* having a double deletion I181+G182+N193F; and further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V

E129V+K177L+R179E+K220P+N224L+S242Q+Q254S (using SEQ ID NO: 1 herein for numbering).

a protease derived from *Pyrococcus furiosus*, preferably the one shown in SEQ ID NO: 13 herein or SEQ ID NO: 29 herein;

a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering); In an embodiment the invention relates to compositions comprising an alpha-amylase derived from *Bacillus stearothermophilus* having a double deletion I181*+G182*+N193F+V59A+Q89R+E129V+K177L+R179E+Q254S+M284V (using SEQ ID NO: 1 herein for numbering).

a protease derived from *Pyrococcus furiosus*, preferably the one in SEQ ID NO: 13 herein or 29 herein;

a *Penicillium oxalicum* glucoamylase shown in SEQ ID NO: 14 having substitutions selected from the group of:

K79V+P11F+T65A+Q327F

K79V+P2N+P4F+P11F+T65A+Q327F (using SEQ ID NO: 14 for numbering).

In an embodiment the *Bacillus stearothermophilus* alpha-amylase (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to the SEQ ID NO: 1.

In an embodiment the *Pyrococcus furiosus* protease (SEQ ID NO: 13 herein or SEQ ID NO: 20 herein) and/or *Thermoascus aurantiacus* protease (SEQ ID NO: 3), or a variant thereof, is the mature protease or corresponding mature protease having at least 80% identity, at least 90% identity, at least 95% identity at least 96% identity at least 97% identity at least 99% identity to the SEQ ID NO: 13 herein or SEQ ID NO: 29 herein, or SEQ ID NO: 3, respectively.

In an embodiment the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity, at least 97%, at least 98% identity, or at least 99% identity to the SEQ ID NO: 14 herein.

In an embodiment the carbohydrate-source generating enzyme, in particular glucoamylase, is derived from a strain of *Penicillium*, such as *Penicillium oxalicum.*

Materials & Methods

Materials:

Alpha-Amylase A (AAA): *Bacillus stearothermophilus* alpha-amylase with the mutations I181*+G182*+N193F truncated to 491 amino acids (SEQ ID NO: 1)

Alpha-Amylase 1407 (AA1407): *Bacillus stearothermophilus* alpha-amylase with the mutations I181*+G182*+N193F+V59A+Q89R+E129V+K177L+R179E+H208Y+K220P+N224L+Q254S truncated to 491 amino acids (SEQ ID NO: 1)

Alpha-Amylase 369 (AA369): *Bacillus stearothermophilus* alpha-amylase with the mutations: I181*+G182*+N193F+V59A+Q89R+E129V+K177L+R179E+Q254S+M284V truncated to 491 amino acids (SEQ ID NO: 1);

Protease 196: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: A27K+D79L+Y82F+S87G+D104P+A112P+A126V+D142L.

Protease Pfu: Protease derived from *Pyrococcus furiosus* purchased from Takara Bio (Japan) as Pfu Protease S (activity 10.5 mg/mL) and also shown in SEQ ID NO: 13 herein.

Protease Pfu2: Protease derived from *Pyrococcus furiosus* shown in SEQ ID NO: 29 herein Glucoamylase PO: Mature part of the *Penicillium oxalicum* glucoamylase disclosed as SEQ ID NO: 2 in PCT/CN10/071753 published as WO 2011/127802 and shown in SEQ ID NO: 9 herein.

Glucoamylase PE001: Variant of the *Penicillium oxalicum* glucoamylase having a K79V substitution using the mature sequence shown in SEQ ID NO: 14 for numbering.

Glucoamylase 493 (GA493): Variant of *Penicillium oxalicum* glucoamylase variant PE001 further having the following substitutions: P11F+T65A+Q327F (using SEQ ID NO: 14 for numbering).

Glucoamylase 498 (GA498): Variant of *Penicillium oxalicum* glucoamylase variant PE001 further having the following substitutions: P2N+P4F+P11F+T65A+Q327F (using SEQ ID NO: 14 for numbering).

Glucoamylase BL: Blend of *Talaromyces emersonii* glucoamylase disclosed in WO 99/28448 as SEQ ID NO: 7 and *Trametes cingulata* glucoamylase disclosed in WO 06/069289 in a ratio of about 9:1.

Glucoamylase BL2: Blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 as side activities (ratio about 65:15:1).

Glucoamylase BL3: Blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 as side activities (ratio about 21:5:1).

Glucoamylase BL4: Blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 with the following substitutions: G128D+D143N (activity ratio AGU:AGU:FAU(F): approx. 30:7:1).

Cellulolytic Composition A (CCA): Cellulase composition from *Trichoderma reesei* sold as CELLUCLAST 1.5 L (Novozymes A/S, Denmark)

Cellulolytic Composition B (CCB): Cellulolytic composition derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 23 herein), *Aspergillus fumigatus* beta-glucosidase (SEQ ID NO: 2 in WO 2005/047499 SEQ ID NO: 22 herein) variant F100D, S283G, N456E, F512Y) disclosed in WO 2012/044915; *Aspergillus fumigatus* Cel7A CBH1 disclosed as SEQ ID NO: 6 in WO2011/057140 (SEQ ID NO: 24 herein) and *Aspergillus fumigatus* CBH II disclosed as SEQ ID NO: 18 in WO 2011/057140 (SEQ ID NO: 25 herein).

Yeast: RED STAR ETHANOL RED™ available from Red Star/Lesaffre, USA.

Substrate in Examples 18 and 19: Ground corn and backset was obtained from a commercial plant in the USA.

Methods

Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences.

The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays

AZCL-Casein Assay

A solution of 0.2% of the blue substrate AZCL-casein is suspended in Borax/$NaH_2PO_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/$NaH_2PO_4$ buffer pH 9.0). The increase in $OD_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

STARCH + IODINE —ALPHA-AMYLASE / 40°, pH 2.5→ DEXTRINS + OLIGOSACCHARIDES

λ = 590 nm blue/violet t = 23 sec.

decoloration

Standard Conditions/Reaction Conditions:

Substrate: Soluble starch, approx. 0.17 g/L

Buffer: Citrate, approx. 0.03 M

Iodine (I2): 0.03 g/L

CaCl2: 1.85 mM pH: 2.50±0.05

Incubation temperature: 40° ° C.

Reaction time: 23 seconds

Wavelength: 590 nm

Enzyme concentration: 0.025 AFAU/mL

Enzyme working range: 0.01-0.04 AFAU/mL

A folder EB-SM-0259.02/01 describing this analytical method in more detail is available upon request to Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of FAU(F)

FAU(F) Fungal Alpha-Amylase Units (Eungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1 numbering)) and alpha-amylase variants thereof was determined by incubating the reference alpha-amylase and variants at pH 4.5 and 5.5 and temperatures of 75° C. and 85° C. with 0.12 mM $CaCl_2$) followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM $CaCl_2$), pH 5.0). Twenty microliters enzyme sample was transferred to 48-well PCR MTP and 180 microliters stability buffer (150 mM acetate, 150 mM MES, 0.01% Triton X100, 0.12 mM $CaCl_2$), pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/ml in residual activity buffer (100 mM Acetate, 0.01% Triton X100, 0.12 mM $CaCl_2$), pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM $CaCl_2$) | T½ (min) (pH 4.5, 85° C., 0.12 mM $CaCl_2$) | T½ (min) (pH 5.5, 85° C., 0.12 mM $CaCl_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |

TABLE 1-continued

| Mutations | T½ (min) (pH 4.5, 75° C., 0.12 mM $CaCl_2$) | T½ (min) (pH 4.5, 85° C., 0.12 mM $CaCl_2$) | T½ (min) (pH 5.5, 85° C., 0.12 mM $CaCl_2$) |
|---|---|---|---|
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |

TABLE 1-continued

| Mutations | T½ (min) (pH 4.5, 75° C., 0.12 mM $CaCl_2$) | T½ (min) (pH 4.5, 85° C., 0.12 mM $CaCl_2$) | T½ (min) (pH 5.5, 85° C., 0.12 mM $CaCl_2$) |
|---|---|---|---|
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability

Strains and Plasmids

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03048353) has been inserted.

*Saccharomyces cerevisiae* YNG318 competent cells: MATa Dpep4[cir+] ura3-52, leu2-D2, his 4-539 was used for protease variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar (2%) and $H_2O$ (approx. 761 ml) is autoclaved together, and the separately sterilized SC-glucose solution is added to the agar solution.

YPD: Bacto peptone 20 g/l, yeast extract 10 g/l, 20% glucose 100 ml/l.

YPD+Zn: YPD+0.25 mM $ZnSO_4$.

PEG/LiAc solution: 40% PEG4000 50 ml, 5 M Lithium Acetate 1 ml.

96 well Zein micro titre plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, NY; Ausubel, F. M. et al. (eds.) "*Current protocols in Molecular Biology*", John Wiley and Sons, 1995; Harwood, C. R. and Cutting, S. M. (Eds.).

Yeast Transformation

Yeast transformation was performed using the lithium acetate method. 0.5 microL of vector (digested by restriction endonucleases) and 1 microL of PCR fragments is mixed. The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Thermoascus* M35 protease gene was amplified with the primer pair Prot F (SEQ ID NO: 4) and Prot R (SEQ ID NO: 5). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO:5) and AM35 (SEQ ID NO:6) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL $H_2O$ | 1 | 94° C. 2 min |
| 2 beads puRe Taq Ready-To-Go PCR (Amersham Biosciences) | 2 | 94° C. 30 sec |
| 0.5 micro L × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex. 60° C. and 65° C., 70° ° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM $ZnSO_4$) and incubated for 4 hours or longer.

After adding 20 microL/well of 100% trichloroacetic acid (TCA) solution, the plate was centrifuge and 100 microL of supernatants were pipette out to measure A440.

Expression of protease variants in *Aspergillus oryzae* The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglucosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al. (2001), *Appl. Environ. Microbiol.* 67, 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

Results

TABLE 2

Relative activity of protease variants. Numbering of substitution(s) starts from N-terminal of the mature peptide in amino acids 1 to 177 of SEQ ID NO: 2.

| Variant | Substitution(s) | Relative activity 65° C./60° C. |
|---|---|---|
| WT | none | 31% |
| JTP004 | S87P | 45% |
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 3

Relative activity of protease variants. Numbering of substitution(s) starts from N-terminal of the mature peptide in amino acids 1 to 177 of SEQ ID NO: 2.

| | | Relative activity | | |
|---|---|---|---|---|
| Variant | Substitution(s) and/or deletion (S) | 70° C./65° C. | 75° C./65° C. | 75° C./70° C. |
| WT | none | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | | 92% |
| JTP055 | ΔG8/D79L/S87P | | | 95% |
| JTP059 | C6R/D79L/S87P | | | 92% |
| JTP061 | T46R/D79L/S87P | | | 111% |
| JTP063 | S49R/D79L/S87P | | | 94% |
| JTP064 | D79L/S87P/N88R | | | 92% |
| JTP068 | D79L/S87P/T114P | | | 99% |
| JTP069 | D79L/S87P/S115R | | | 103% |
| JTP071 | D79L/S87P/T116V | | | 105% |
| JTP072 | N26R/D79L/S87P | | 92% | |
| JTP077 | A27K/D79L/S87P/A112P/D142L | | 106% | |
| JTP078 | A27V/D79L/S87P/A112P/D142L | | 100% | |
| JTP079 | A27G/D79L/S87P/A112P/D142L | | 104% | |

TABLE 4

Relative activity of protease variants. Numbering of substitution(s) starts from N-terminal of the mature peptide in amino acids 1 to 177 of SEQ ID NO: 2.

| | | Relative activity | Remaining activity | |
|---|---|---|---|---|
| Variant | Substitution(s) and/or deletion(s) | 75° C./65° C. | 80° C. | 84° C. |
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | | 60% |
| JTP095 | N26R/T46R/D79L/S87P/A112P/D142L | | | 62% |
| JTP096 | T46R/D79L/S87P/T116V/D142L | | | 67% |
| JTP099 | D79L/P81R/S87P/A112P/D142L | | | 80% |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 5

Relative activity of protease variants. Numbering of substitution(s) starts from N-terminal of the mature peptide in amino acids 1 to 177 of SEQ ID NO: 2.

| | | Relative activity | | |
|---|---|---|---|---|
| Variant | Substitutions | 75° C./70° C. | 80° C./70° C. | 85° C./70° C. |
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |

TABLE 5-continued

Relative activity of protease variants. Numbering of substitution(s) starts from N-terminal of the mature peptide in amino acids 1 to 177 of SEQ ID NO: 2.

| | | Relative activity | | |
|---|---|---|---|---|
| Variant | Substitutions | 75° C./70° C. | 80° C./70° C. | 85° C./70° C. |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87G A112P D142L | | 30% | 12% |
| JTP180 | S70V D79L Y82F S87G Y97W A112P D142L | | 52% | |
| JTP181 | D79L Y82F S87G Y97W D104P A112P D142L | | 45% | |
| JTP187 | S70V D79L Y82F S87G A112P D142L | | 45% | |
| JTP188 | D79L Y82F S87G D104P A112P D142L | | 43% | |
| JTP189 | D79L Y82F S87G A112P A126V D142L | | 46% | |
| JTP193 | Y82F S87G S70V D79L D104P A112P D142L | | | 15% |
| JTP194 | Y82F S87G D79L D104P A112P A126V D142L | | | 22% |
| JTP196 | A27K D79L Y82F S87G D104P A112P A126V D142L | | | 18% |

TABLE 5

Relative activity of protease variants. Numbering of substitution(s) starts from N-terminal of the mature peptide in amino acids 1 to 177 of SEQ ID NO: 2.

| | | Relative activity | |
|---|---|---|---|
| Variant | Substitutions | 75° C./70° C. | 80° C./70° C. |
| JTP196 | A27K D79L Y82F S87G D104P A112P A126V D142L | 102% | 55% |
| JTP210 | A27K Y82F S87G D104P A112P A126V D142L | 107% | 36% |
| JTP211 | A27K D79L Y82F D104P A112P A126V D142L | 94% | 44% |
| JTP213 | A27K Y82F D104P A112P A126V D142L | 103% | 37% |

Example 3

Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:

1) Mix 10 μl of 10 ug/ml enzyme solutions and 100 μl of 0.025% zein solution in a micro titer plate (MTP).
2) Incubate at various temperatures for 60 min.
3) Add 10 μl of 100% trichloroacetic acid (TCA) solution.
4) Centrifuge MTP at 3500 rpm for 5 min.
5) Take out 15 μl to a new MTP containing 100 μl of BCA assay solution (Pierce Cat #:23225, BCA Protein Assay Kit).
6) Incubate for 30 min. at 60° C.
7) Measure A562.

The results are shown in Table 6. All of the tested variants showed an improved thermo-stability as compared to the wt protease.

TABLE 6

Zein-BCA assay

| | Sample incubated 60 min at indicated temperatures (° C.) (μg/ml Bovine serum albumin equivalent peptide released) | | | | | | |
|---|---|---|---|---|---|---|---|
| WT/Variant | 60° C. | 70° C. | 75° C. | 80° C. | 85° C. | 90° C. | 95° C. |
| WT | 94 | 103 | 107 | 93 | 58 | 38 | |
| JTP050 | 86 | 101 | 107 | 107 | 104 | 63 | 36 |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

Example 4

Characterization of *Penicillium oxalicum* Glucoamylase

The *Penicillium oxalicum* glucoamylase is disclosed in SEQ ID NO: 9 herein.

Substrate. Substrate: 1% soluble starch (Sigma S-9765) in deionized water

Reaction buffer: 0.1 M Acetate buffer at pH 5.3

Glucose concentration determination kit: Wako glucose assay kit (LabAssay glucose, WAKO, Cat #298-65701).

Reaction condition. 20 microL soluble starch and 50 microL acetate buffer at pH 5.3 were mixed. 30 microL enzyme solution (50 micro g enzyme protein/ml) was added to a final volume of 100 microL followed by incubation at 37° C. for 15 min.

The glucose concentration was determined by Wako kits.

All the work carried out in parallel.

Temperature optimum. To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 7.

TABLE 7

| Temperature optimum | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability. To assess the heat stability of the *Penicillium oxalicum* glucoamylase the Reaction condition assay was modified in that the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 8.

TABLE 8

| Heat stability | | | | | | | | | | |
|---|---|---|---|---|---|---|---|---|---|---|
| | Temperature (° C.) | | | | | | | | | |
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$), 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 9.

TABLE 9

| pH optimum | | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH stability. To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 10.

TABLE 10

| pH stability | | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Thermostability of Protease Pfu.

The thermostability of the *Pyrococcus furiosus* protease (Pfu S) purchased from Takara Bio Inc, (Japan) was tested using the same methods as in Example 2. It was found that the thermostability (Relative Activity) was 110% at (80° C./70° C.) and 103% (90° C./70° C.) at pH 4.5.

Example 6

Cloning of *Penicillium oxalicum* Strain Glucoamylase Gene

Preparation of *Penicillium oxalicum* Strain cDNA.

The cDNA was synthesized by following the instruction of 3' Rapid Amplification of cDNA End System (Invitrogen Corp., Carlsbad, CA, USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
Sense primer:
                                   (SEQ ID NO: 15)
5'-ATGCGTCTCACTCTATTATCAGGTG-3'
```

The full length gene was amplified by PCR with Sense primer and AUAP (supplied by 3' Rapid Amplification of cDNA End System) by using Platinum HIFI Taq DNA polymerase (Invitrogen Corp., Carlsbad, CA, USA). The amplification reaction was composed of 5 μl of 10×PCR buffer, 2 μl of 25 mM $MgCl_2$, 1 μl of 10 mM dNTP, 1 μl of 10 μM Sense primer, 1 μl of 10 μM AUAP, 2 μl of the first strand cDNA, 0.5 μl of HIFI Taq, and 37.5 μl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° ° C. for 40 secs, 68° C. for 2 min; final extension at 68° C. for 10 mins.

The obtained PCR fragment was cloned into pGEM-T vector (Promega Corporation, Madison, WI, USA) using a pGEM-T Vector System (Promega Corporation, Madison, WI, USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen und Zellkulturen GmbH (DSMZ) on Nov. 23, 2009, and assigned accession number as DSM 23123.

Example 7

Expression of Cloned *Penicillium oxalicum* Glucoamylase

The *Penicillium oxalicum* glucoamylase gene was recloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                          (SEQ ID NO: 16)
5' ACACAACTGGGGATCCACCATGCGTCTCACTCTATTATC

Primer R:
                                          (SEQ ID NO: 17)
5' AGATCTCGAGAAGCTTAAAACTGCCACACGTCGTTGG
```

A PCR reaction was performed with plasmid AMG 1 in order to amplify the full-length gene. The PCR reaction was composed of 40 μg of the plasmid AMG 1 DNA, 1 μl of each primer (100 μM); 12.5 μl of 2× Extensor Hi-Fidelity master mix (Extensor Hi-Fidelity Master Mix, ABgene, United Kingdom), and 9.5 μl of PCR-grade water. The PCR reaction was performed using a DYAD PCR machine (Bio-Rad Laboratories, Inc., Hercules, CA, USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, CA, USA) according to the manufacturer's instructions. The linearized vector construction is as described in WO 2005/042735 A1.

A 2 μl volume of the ligation mixture was used to transform 25 μl of Fusion Blue *E. coli* cells (included in the IN-FUSION™ Dry-Down PCR Cloning Kit). After a heat shock at 42° C. for 45 sec, and chilling on ice, 250 μl of SOC medium was added, and the cells were incubated at 37° C. at 225 rpm for 90 min before being plated out on LB agar plates containing 50 μg of ampicillin per ml, and cultivated overnight at 37° C. Selected colonies were inoculated in 3 ml of LB medium supplemented with 50 μg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MBin118 were prepared as described in WO 95/02043. One hundred μl of protoplast suspension were mixed with 2.5 μg of the XYZ1471-4 plasmid and 250 microliters of 60% PEG 4000 (Applichem) (polyethylene glycol, molecular weight 4,000), 10 mM $CaCl_2$), and 10 mM Tris-HCl PH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamide and 15 mM CsCl and added as a top layer on COVE sucrose (1M) plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation. The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 μm membrane filters.

Alpha-cyclodextrin affinity gel. Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of glucoamylase from culture broth. Culture broth from fermentation of *A. niger* MBin118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 8

Construction and Expression of a Site-Directed Variant of *Penicillium oxalicum* Glucoamylase Two PCR reactions were performed with plasmid XYZ1471-4, described in Example 7, using primers K79V F and K79VR shown below, which were designed to substitute lysine K at position 79 from the mature sequence to valine (V) and primers F-NP003940 and R-NP003940 shown below, which were designed based on the known sequence and added tags for direct cloning by IN-FUSION™ strategy.

```
Primer K79V F 18mer
                                        (SEQ ID NO: 18)
GCAGTCTTTCCAATTGAC

Primer K79V R 18mer
                                        (SEQ ID NO: 19)
AATTGGAAAGACTGCCCG

Primer F-NP003940:
                                        (SEQ ID NO: 20)
5' ACACAACTGGGGATCCACCATGCGTCTCACTCTATTATC

Primer R-NP003940:
                                        (SEQ ID NO: 21)
5' AGATCTCGAGAAGCTTAAAACTGCCACACGTCGTTGG
```

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To-Go PCR Beads (Amersham Biosciences) | 2 | 94° C. 30 sec |
| | 3 | 55° C. 30 sec |
| 0.5 micro L × 2100 pmole/micro L Primers | 4 | 72° C. 90 sec |
| (K79V F + Primer R-NP003940, K79V R + Primer F-NP003940) | 2-4 | 25 cycles |
| | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, CA, USA) according to the manufacturer's instructions. The linearized vector construction is as described in WO 2005/042735 A1.

The ligation mixture was used to transform *E. coli* DH5a cells (TOYOBO). Selected colonies were inoculated in 3 ml of LB medium supplemented with 50 μg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MBin118 were prepared as described in WO 95/02043. One hundred μl of protoplast suspension were mixed with 2.5 μg of the pPoPE001 plasmid and 250 microliters of 60% PEG 4000 (Applichem) (polyethylene glycol, molecular weight 4,000), 10 mM $CaCl_2$), and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamide and 15 mM CsCl and added as a top layer on COVE sucrose plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE gel in order to identify the best transformants based on the ability to produce large amount of the glucoamylase.

Example 9

Purification of Site-Directed Po AMG Variant PE001

The selected transformant of the variant and the strain expressing the wild type *Penicillium oxalicum* glucoamylase described in Example 6 was cultivated in 100 ml of YP-2% maltose medium and the culture was filtrated through a 0.22 μm PES filter, and applied on a alpha-cyclodextrin affinity gel column previously equilibrated in 50 mM NaOAc, 150 mM NaCl, pH 4.5 buffer. Unbound materials was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 10

Characterization of PE001 Protease stability

40 μl enzyme solutions (1 mg/ml) in 50 mM sodium acetate buffer, pH 4.5, were mixed with 1/10 volume of 1 mg/ml protease solutions such as aspergillopepsin I described in Biochem J. 1975 April; 147(1):45-53, or the commercially available product from Sigma and aorsin described in Biochemical journal [0264-6021] Ichishima yr: 2003 vol:371 iss:Pt 2 pg:541 and incubated at 4 or 32° C. overnight. As a control experiment, $H_2O$ was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

TABLE 11

The result of SDS-PAGE after protease treatment

| | Wild type glucoamylase | | | | PE001 | | | | |
|---|---|---|---|---|---|---|---|---|---|
| Protease | aspergillopepsin I | | aorsin | | aspergillopepsin I | | aorsin | | control |
| Incubation temperature (° C.) | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D | N.D | N.D. |

N.D.: not detected.

Example 11

Less Cleavage During Cultivation

*Aspergillus* transformant of the variant and the wild type *Penicillium oxalicum* glucoamylase were cultivated in 6-well MT plates containing 4× diluted YP-2% maltose medium supplemented with 10 mM sodium acetate buffer, pH4.5, at 32° C. for 1 week.

The culture supernatants were loaded on SDS-PAGE.

TABLE 12

The result of SDS-PAGE of the culture supernatants

| | Wild type glucoamylase | PE001 |
|---|---|---|
| intact glucoamylase (ca. 70 kDa) | 90% | 100% |
| cleaved glucoamylase (ca. 60 kDa) | 10% | N.D. |

N.D.: not detected.

The wild type glucoamylase was cleaved by host proteases during fermentation, while the variant yielded only intact molecule.

Example 12

Glucoamylase Activity of Variant Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 13

| Relative specific activity | AGU/mg |
|---|---|
| *Penicillium oxalicum* wt | 100% |
| *Penicillium oxalicum* PE001 (SEQ ID NO: 14 + K79V substitution) | 102% |

Example 13

Purification of Glucoamylase Variants Having Increased Thermostability

The variants showing increased thermostability may be constructed and expressed similar to the procedure described in Example 8. All variants were derived from the PE001. After expression in YPM medium, variants comprising the T65A or Q327F substitution was micropurified as follows:

Mycelium was removed by filtration through a 0.22 μm filter. 50 μl column material (alpha-cyclodextrin coupled to Mini-Leak divinylsulfone-activated agarose medium according to manufacturer's recommendations) was added to the wells of a filter plate (Whatman, Unifilter 800 μl, 25-30 μm MBPP). The column material was equilibrated with binding buffer (200 mM sodium acetate pH 4.5) by two times addition of 200 μl buffer, vigorous shaking for 10 min (Heidolph, Titramax 101, 1000 rpm) and removal of buffer by vacuum (Whatman, UniVac 3). Subsequently, 400 μl culture supernatant and 100 μl binding buffer was added and the plate incubated 30 min with vigorous shaking. Unbound material was removed by vacuum and the binding step was repeated. Normally 4 wells were used per variant. Three washing steps were then performed with 200 μl buffer of decreasing ionic strength added (50/10/5 mM sodium acetate, pH 4.5), shaking for 15 min and removal of buffer by vacuum. Elution of the bound AMG was achieved by two times addition of 100 μl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 14

Protein Thermal Unfolding Analysis (TSA, Thermal Shift Assay).

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4.5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76° C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4.5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dk) (ref.: Gregory et al; *J Biomol Screen* 2009 14: 700.)

TABLE 14a

| Sample | Tm (Deg. Celsius) +/− 0.4 |
|---|---|
| PO-AMG (PE001) | 80.3 |
| Variant Q327F | 82.3 |
| Variant T65A | 81.9 |

TABLE 14b

| Sample | Tm (Deg. Celsius) +/− 0.4 | |
|---|---|---|
| Acarbose: | − | + |
| PO-AMG (PE001) | 79.5 | 86.9 |
| Variant E501V Y504T | 79.5 | 95.2 |

Example 15

Thermostability Analysis by Differential Scanning Calorimetry (DSC)

Additional site specific variants having substitutions and/or deletions at specific positions were constructed basically as described in Example 8 and purified as described in Example 11.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, NJ, USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 15 below.

TABLE 15

| Po-AMG name | Mutations | DSC Td (° C.) @ pH 4.0 | DSC Td (° C.) @ pH 4.8 |
|---|---|---|---|
| PE001 (SEQ ID NO: 14 + K79V) | | 82.1 | 83.4 |
| GA167 | E501V Y504T | 82.1 | |
| GA481 | T65A K161S | 84.1 | 86.0 |
| GA487 | T65A Q405T | 83.2 | |
| GA490 | T65A Q327W | 87.3 | |
| GA491 | T65A Q327F | 87.7 | |
| GA492 | T65A Q327Y | 87.3 | |
| GA493 | P11F T65A Q327F | 87.8 | 88.5 |
| GA497 | R1K D3W K5Q G7V N8S T10K P11S T65A Q327F | 87.8 | 88.0 |
| GA498 | P2N P4S P11F T65A Q327F | 88.3 | 88.4 |
| GA003 | P11F D26C K33C T65A Q327F | 83.3 | 84.0 |
| GA009 | P2N P4S P11F T65A Q327W E501V Y504T | 88.8 | |
| GA002 | R1E D3N P4G G6R G7A N8A T10D P11D T65A Q327F | 87.5 | 88.2 |
| GA005 | P11F T65A Q327W | 87.4 | 88.0 |

TABLE 15-continued

| Po-AMG name | Mutations | DSC Td (° C.) @ pH 4.0 | DSC Td (° C.) @ pH 4.8 |
|---|---|---|---|
| GA008 | P2N P4S P11F T65A Q327F E501V Y504T | 89.4 | 90.2 |
| GA010 | P11F T65A Q327W E501V Y504T | | 89.7 |
| GA507 | T65A Q327F E501V Y504T | | 89.3 |
| GA513 | T65A S105P Q327W | | 87.0 |
| GA514 | T65A S105P Q327F | | 87.4 |
| GA515 | T65A Q327W S364P | | 87.8 |
| GA516 | T65A Q327F S364P | | 88.0 |
| GA517 | T65A S103N Q327F | | 88.9 |
| GA022 | P2N P4S P11F K34Y T65A Q327F | | 89.7 |
| GA023 | P2N P4S P11F T65A Q327F D445N V447S | | 89.9 |
| GA032 | P2N P4S P11F T65A I172V Q327F | | 88.7 |
| GA049 | P2N P4S P11F T65A Q327F N502* | | 88.4 |
| GA055 | P2N P4S P11F T65A Q327F N502T P563S K571E | | 88.0 |
| GA057 | P2N P4S P11F R31S K33V T65A Q327F N564D K571S | | 89.5 |
| GA058 | P2N P4S P11F T65A Q327F S377T | | 88.6 |
| GA064 | P2N P4S P11F T65A V325T Q327W | | 88.0 |
| GA068 | P2N P4S P11F T65A Q327F D445N V447S E501V Y504T | | 90.2 |
| GA069 | P2N P4S P11F T65A I172V Q327F E501V Y504T | | 90.2 |
| GA073 | P2N P4S P11F T65A Q327F S377T E501V Y504T | | 90.1 |
| GA074 | P2N P4S P11F D26N K34Y T65A Q327F | | 89.1 |
| GA076 | P2N P4S P11F T65A Q327F I375A E501V Y504T | | 90.2 |
| GA079 | P2N P4S P11F T65A K218A K221D Q327F E501V Y504T | | 90.9 |
| GA085 | P2N P4S P11F T65A S103N Q327F E501V Y504T | | 91.3 |
| GA086 | P2N P4S T10D T65A Q327F E501V Y504T | | 90.4 |
| GA088 | P2N P4S F12Y T65A Q327F E501V Y504T | | 90.4 |
| GA097 | K5A P11F T65A Q327F E501V Y504T | | 90.0 |
| GA101 | P2N P4S T10E E18N T65A Q327F E501V Y504T | | 89.9 |
| GA102 | P2N T10E E18N T65A Q327F E501V Y504T | | 89.8 |
| GA084 | P2N P4S P11F T65A Q327F E501V Y504T T568N | | 90.5 |
| GA108 | P2N P4S P11F T65A Q327F E501V Y504T K524T G526A | | 88.6 |
| GA126 | P2N P4S P11F K34Y T65A Q327F D445N V447S E501V Y504T | | 91.8 |
| GA129 | P2N P4S P11F R31S K33V T65A Q327F D445N V447S E501V Y504T | | 91.7 |
| GA087 | P2N P4S P11F D26N K34Y T65A Q327F E501V Y504T | | 89.8 |
| GA091 | P2N P4S P11F T65A F80* Q327F E501V Y504T | | 89.9 |
| GA100 | P2N P4S P11F T65A K112S Q327F E501V Y504T | | 89.8 |
| GA107 | P2N P4S P11F T65A Q327F E501V Y504T T516P K524T G526A | | 90.3 |
| GA110 | P2N P4S P11F T65A Q327F E501V N502T Y504* | | 90.6 |

Example 16

Thermostability Analysis by Thermo-Stress Test and pNPG Assay

Starting from one of the identified substitution variants from Example 15, identified as GA008, additional variants were tested by a thermo-stress assay in which the supernatant from growth cultures were assayed for glucoamylase (AMG) activity after a heat shock at 83° C. for 5 min.

After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thermo-stressed and non-thermo-stressed. The data output is therefore a measurement of residual activity in the stressed samples.

Growth:

A sterile micro titer plate (MTP) was added 200 μL rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 μL supernatant was transferred to 50 μL 0.5 M NaAc pH 4.8 to obtain correct sample pH.

50 μL dilution was transferred to a PCR plate and thermo-stressed at 83° C. for 5 minutes in a PCR machine. The remaining half of the dilution was kept at RT.

20 μL of both stressed and unstressed samples was transferred to a standard MTP. 20 μL pNPG-substrate was added to start the reaction. The plate was incubated at RT for 1 hour.

The reaction was stopped and the colour developed by adding 50 μL 0.5M $Na_2CO_3$. The yellow colour was measured on a plate reader (Molecular Devices) at 405 nm.

Buffers:

0.5 M NaAc pH 4.8

0.25 M NaAc pH 4.8

Substrate, 6 mM pNPG:

15 mg 4-nitrophenyl D-glucopyranoside in 10 mL 0.25 NaAc pH 4.8

Stop/Developing Solution:

0.5 M $Na_2CO_3$

Data Treatment:

In Excel the raw Abs405 data from both stressed and unstressed samples were blank subtracted with their respective blanks. The residual activity (% res. act.=($Abs_{unstressed}$−($Abs_{unstressed}$−$Abs_{stressed}$))/$Abs_{unstressed}$*100%) was calculated and plotted relative to benchmark, Po-amg0008.

TABLE 16

| Po-AMG name | Mutations | % residual activity |
|---|---|---|
| GA008 | P2N P4S P11F T65A Q327F E501V Y504T | 100 |
| GA085 | P2N P4S P11F T65A S103N Q327F E501V Y504T | 127 |
| GA097 | K5A P11F T65A Q327F E501V Y504T | 106 |
| GA107 | P2N P4S P11F T65A Q327F E501V Y504T T516P K524T G526A | 109 |
| GA130 | P2N P4S P11F T65A V79A Q327F E501V Y504T | 111 |
| GA131 | P2N P4S P11F T65A V79G Q327F E501V Y504T | 112 |
| GA132 | P2N P4S P11F T65A V79I Q327F E501V Y504T | 101 |
| GA133 | P2N P4S P11F T65A V79L Q327F E501V Y504T | 102 |
| GA134 | P2N P4S P11F T65A V79S Q327F E501V Y504T | 104 |

TABLE 16-continued

| Po-AMG name | Mutations | % residual activity |
|---|---|---|
| GA150 | P2N P4S P11F T65A L72V Q327F E501V Y504T | 101 |
| GA155 | S255N Q327F E501V Y504T | 105 |

TABLE 17

| Po-AMG name | Mutations | % residual activity |
|---|---|---|
| GA008 | P2N P4S P11F T65A Q327F E501V Y504T | 100 |
| GA179 | P2N P4S P11F T65A E74N V79K Q327F E501V Y504T | 108 |
| GA180 | P2N P4S P11F T65A G220N Q327F E501V Y504T | 108 |
| GA181 | P2N P4S P11F T65A Y245N Q327F E501V Y504T | 102 |
| GA184 | P2N P4S P11F T65A Q253N Q327F E501V Y504T | 110 |
| GA185 | P2N P4S P11F T65A D279N Q327F E501V Y504T | 108 |
| GA186 | P2N P4S P11F T65A Q327F S359N E501V Y504T | 108 |
| GA187 | P2N P4S P11F T65A Q327F D370N E501V Y504T | 102 |
| GA192 | P2N P4S P11F T65A Q327F V460S E501V Y504T | 102 |
| GA193 | P2N P4S P11F T65A Q327F V460T P468T E501V Y504T | 102 |
| GA195 | P2N P4S P11F T65A Q327F T463N E501V Y504T | 103 |
| GA196 | P2N P4S P11F T65A Q327F S465N E501V Y504T | 106 |
| GA198 | P2N P4S P11F T65A Q327F T477N E501V Y504T | 106 |

Example 17

Test for Glucoamylase Activity of Thermo-Stable Variants According to the Invention All of the above described variants disclosed in tables 15, 16, and 17 have been verified for Glucoamylase activity on culture supernatants using the pNPG assay described in Example 16.

Example 18

Ethanol Production Using Alpha-Amylase a (AAA), Protease 196, and Glucoamylase 493 (GA493) for Liquefaction and Glucoamylase BL3 (BL3) and Cellulolytic Composition a (CCA) for Fermentation Liquefaction (Labomat)

Each liquefaction received ground corn (86.3% DS), backset (7.2% DS), and tap water targeting a total weight of 150 g at 32.50% Dry Solids (DS). Backset was blended at 30% w/w of total slurry weight. Initial slurry pH was 5.2 and was therefore not adjusted before liquefaction. All enzymes were added according to the table below.

| | Alpha-Amylase A | Protease 196 | Glucoamylase GA493 |
|---|---|---|---|
| Mash #1 | 0.02% w/w corn as is | none | none |
| Mash #2 | 0.02% w/w corn as is | 0.001 JTPU/g DS | 6 mcg/g DS |

Liquefaction took place in a Labomat using the following conditions: 5° C./min. Ramp, 17 minute Ramp, 103 minute hold time at 85° C., 40 rpm for the entire run, 200 mL stainless steel canisters. After liquefaction, all canisters were cooled in an ice bath and prepared for fermentation based on the protocol listed below under SSF.

Simultaneous Saccharification and Fermentation (SSF)

Two mashes above were adjusted to pH 5.0 with 50% w/w Sodium Hydroxide or 40% v/v sulfuric acid. Penicillin was applied to each mash to a total concentration of 3 ppm, and urea was added to each mash as nitrogen source to a final concentration of 1000 ppm. The tubes were prepared with mash by aliquoting approximately 4.5 g of mash per 15 mL pre-drilled test tubes to allow $CO_2$ release. Novozymes glucoamylase Spirizyme Excel and cellulase Celluclast were dosed into the tubes according to the following table:

| Treatment # | Mash | Glucoamylase | AMG Dosage AGU/g DS | Cellulolytic Composition (CC) | Cellulase Dosage mg EP/g DS |
|---|---|---|---|---|---|
| 1 | Mash #1 | BL3 | 0.60 | — | — |
| 2 | Mash #1 | BL3 | 0.60 | A | 0.10 |
| 3 | Mash #2 | BL3 | 0.60 | — | — |
| 4 | Mash #2 | BL3 | 0.60 | A | 0.10 |

Distilled water was added to each tube in the appropriate volume to keep the solids at the same concentration in all tubes. All treatments were conducted in five replicates. After enzyme dosage, each tube received 100 μL of rehydrated yeast. Rehydrated yeast was prepared by mixing 5.5 g of Fermentis RED STAR into 100 mL of tap water and incubating at 32° C. for about 30 minutes. All the tubes were vortexed, and then incubated in 32° C. water bath for 52 hours in the SSF process.

Fermentation sampling took place after 52 hours of fermentation. Each sample was deactivated with 50 μL of 40% v/v $H_2SO_4$, vortexing, centrifuging at 3000 rpm for 10 minutes, and filtering through a 0.45 μm Whatman PP filter. All samples were analyzed by HPLC.

Results:

| Treatment | Ethanol (g/L) | Std Dev. | CV |
|---|---|---|---|
| AAA + BL3 | 124.48 | 0.0257 | 0.21% |
| AAA + BL3 + CCA | 125.21 | 0.0358 | 0.29% |
| AAA + Protease196 + GA493 + BL3 | 125.16 | 0.0317 | 0.25% |
| AAA + Protease196 + GA493 + BL3 + CCA | 125.43 | 0.0495 | 0.39% |

With Cellulolytic Composition A (CCA) addition into the SSF process, there was a 0.73 g/L ethanol yield increase from the corn mash liquefied by Alpha-Amylase A (AAA). When adding Protease196 and Glucoamylase 493 (GA493) together with Alpha-amylase A into the liquefaction, and adding Cellulolytic Composition A (CCA) into SSF, the total ethanol yield was increased by 1 g/L.

Example 19

Ethanol Production Using Alpha-Amylase a or Alpha-Amylase AA369, Protease Pfu2 and Glucoamylase 498 (GA498) for Liquefaction, and Glucoamylase BL4 with Cellulolytic Composition A or B (CCA or CCB) for Fermentation Liquefaction (Labomat)

Each liquefaction received ground corn (86.3% DS), backset (7.2% DS), and tap water targeting a total weight of 375 g at 32.50% Dry Solids (DS). Backset was blended at 30% w/w of total slurry weight. Initial slurry pH was adjusted before liquefaction. All enzymes were added according to the table below.

| | Amylase and Dose | Protease and dose | Glucoamylase and dose |
|---|---|---|---|
| Mash #1 | LSCDS | none | none |
| pH 5.8 | 0.024% w/w corn as is | | |
| Mash #2 | AA369 | PFU2 | GA498 |
| pH 5.2 | 2.14 μg/g DS | 0.0385 μg/g DS | 4.5 μg/g DS |

Liquefaction took place in a Labomat using the following conditions: In 200 mL stainless steel canisters increase temperature by 5° C./min up to 80° C.; hold 2 min, then 2° C./min up to 85° C.; hold at 85° C. for 103 min. After liquefaction, all mashes were stored frozen until they were prepared for fermentation based on the protocol listed below under SSF.

Simultaneous Saccharification and Fermentation (SSF)

Each mash above was adjusted to pH 5.0 with 50% w/w Sodium Hydroxide or 40% v/v sulfuric acid. Penicillin was applied to each mash to a total concentration of 3 ppm, and urea was added to each mash as nitrogen source to a final concentration of 800 ppm. Solids content of both mashes was adjusted to 30% by addition of water. The tubes were prepared with mash by aliquoting approximately 4.5 g of mash per 15 mL pre-drilled test tubes to allow $CO_2$ release. Glucoamylase BL4 and Cellulolytic Composition CCA or CCB were dosed into the tubes according to the following table:

| Treatment # | Mash | Glucoamylase | AMG Dosage AGU/g DS | Cellulolytic Composition (CC) | Cellulase Dosage mg EP/g DS |
|---|---|---|---|---|---|
| 1 | Mash #1 | BL4 | 0.60 | none | 0 |
| 2 | Mash #1 | BL4 | 0.60 | CCB | 0.05 |
| 3 | Mash #1 | BL4 | 0.60 | CCB | 0.15 |
| 4 | Mash #1 | BL4 | 0.60 | CCB | 0.3 |
| 5 | Mash #1 | BL4 | 0.60 | CCA | 0.05 |
| 6 | Mash #1 | BL4 | 0.60 | CCA | 0.15 |
| 7 | Mash #1 | BL4 | 0.60 | CCA | 0.3 |
| 8 | Mash #2 | BL4 | 0.60 | none | 0 |
| 9 | Mash #2 | BL4 | 0.60 | CCB | 0.05 |
| 10 | Mash #2 | BL4 | 0.60 | CCB | 0.15 |
| 11 | Mash #2 | BL4 | 0.60 | CCB | 0.3 |
| 12 | Mash #2 | BL4 | 0.60 | CCA | 0.05 |
| 13 | Mash #2 | BL4 | 0.60 | CCA | 0.15 |
| 14 | Mash #2 | BL4 | 0.60 | CCA | 0.3 |

Distilled water was added to each tube in the appropriate volume to keep the solids at the same concentration in all tubes. All treatments were conducted in five replicates. After enzyme dosage, each tube received 100 μL of rehydrated yeast. Rehydrated yeast was prepared by mixing 5.5 g of Fermentis RED STAR into 100 mL of tap water and incubated at 32° C. for about 30 minutes. All the tubes were vortexed, and then incubated in 32° C. water bath for 51 hours in the SSF process.

Fermentation sampling took place after 51 hours of fermentation. Each sample was deactivated with 50 μL of 40% v/v $H_2SO_4$, vortexing, centrifuging at 3000 rpm for 10 minutes, and filtering through a 0.45 μm Whatman PP filter. All samples were analyzed by HPLC.

Results:

| Treatment | Ethanol (g/L) | Std Dev. | CV |
|---|---|---|---|
| AAA + BL4 | 114.99 | 0.67 | 0.58% |
| AAA + BL4 + CCB 0.05 | 116.08 | 0.87 | 0.75% |
| AAA + BL4 + CCB 0.15 | 117.17 | 0.86 | 0.73% |
| AAA + BL4 + CCB 0.3 | 117.61 | 0.92 | 0.78% |
| AAA + BL4 + CCA0.05 | 115.53 | 0.76 | 0.65% |
| AAA + BL4 + CCA 0.15 | 115.46 | 0.92 | 0.79% |
| AAA + BL4 + CCA 0.3 | 115.84 | 0.79 | 0.68% |
| AA369 + GA498 + Pfu2 + BL4 | 115.51 | 0.68 | 0.59% |
| AA369 + GA498 + Pfu2 + BL4 + CCB 0.05 | 116.70 | 0.64 | 0.55% |
| AA369 + GA498 + Pfu2 + BL4 + CCB 0.15 | 117.31 | 0.86 | 0.73% |
| AA369 + GA498 + Pfu2 + BL4 + CCB 0.3 | 118.74 | 0.72 | 0.61% |
| AA369 + GA498 + Pfu2 + BL4 + CCA 0.05 | 116.90 | 0.36 | 0.31% |
| AA369 + GA498 + Pfu2 + BL4 + CCA 0.15 | 117.38 | 0.88 | 0.75% |
| AA369 + GA498 + Pfu2 + BL4 + CCA 0.3 | 116.99 | 0.27 | 0.23% |

With Cellulolytic Composition A (CCA) addition into the SSF process, there was an ethanol yield increase of up to 0.74% compared to the corn mash liquefied by Alpha-Amylase A (AAA) with no added Cellulolytic Composition in fermentation. With Cellulolytic Composition B (CCB) in the same mash, there was an ethanol yield increase of up to 2.28%.

When adding Protease Pfu2 and Glucoamylase 498 (GA498) together with Alpha-amylase 369 into the liquefaction, and adding Cellulolytic Composition A (CCA) into SSF, the total ethanol yield was increased by up to 1.62% compared to the same mash with no added Cellulolytic Composition. With Cellulolytic Composition B (CCB) in the same mash, there was an ethanol yield increase of up to 2.80%.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described in the following numbered paragraphs:

1. A process for producing fermentation products from starch-containing material comprising the steps of:

i) liquefying the starch-containing material at a temperature above the initial gelatinization temperature using:

an alpha-amylase;

optionally a protease having a thermostability value of more than 20% determined as Relative Activity at 80° C./70° C.; and optionally a carbohydrate-source generating enzyme;

ii) saccharifying using a carbohydrate-source generating enzyme;

iii) fermenting using a fermenting organism;

wherein a cellulolytic composition is present or added during fermentation or simultaneous saccharification and fermentation.

2. The process of paragraph 1, further comprises, prior to the liquefaction step i), the steps of:

a) reducing the particle size of the starch-containing material, preferably by dry milling;

b) forming a slurry comprising the starch-containing material and water.

3. The process of any of paragraphs 1-2, wherein at least 50%, preferably at least 70%, more preferably at least 80%, especially at least 90% of the starch-containing material fit through a sieve with #6 screen.

4. The process of any of paragraphs 1-3, wherein the pH during liquefaction is from 4.5-5.0, such as between 4.5-4.8.

5. The process of any of paragraphs 1-3, wherein the pH during liquefaction is between above 5.0-6.5, such as above 5.0-6.0, such as above 5.0-5.5, such as between 5.2-6.2, such as around 5.2, such as around 5.4, such as around 5.6, such as around 5.8.

6. The process of any of paragraphs 1-5, wherein the temperature during liquefaction is in the range from 70-100° C., such as between 75-95° C., such as between 75-90° C., preferably between 80-90° C., such as 82-88° C., such as around 85° C.

7. The process of any of paragraphs 1-6, wherein a jet-cooking step is carried out after liquefaction in step i).

8. The process of paragraph 7, wherein the jet-cooking is carried out at a temperature between 110-145° ° C., preferably 120-140° C., such as 125-135° C., preferably around 130° C. for about 1-15 minutes, preferably for about 3-10 minutes, especially around about 5 minutes.

9. The process of any of paragraphs 1-8, wherein saccharification and fermentation is carried out sequentially or simultaneously.

10. The process of any of paragraphs 1-9, wherein saccharification is carried out at a temperature from 20-75° C., preferably from 40-70° C., such as around 60° C., and at a pH between 4 and 5.

11. The process of any of paragraphs 1-10, wherein fermentation or simultaneous saccharification and fermentation (SSF) is carried out carried out at a temperature from 25° ° C. to 40° C., such as from 28° C. to 35° C., such as from 30° C. to 34° C., preferably around about 32° C. In an embodiment fermentation is ongoing for 6 to 120 hours, in particular 24 to 96 hours.

12. The process of any of paragraphs 1-11, wherein the fermentation product is recovered after fermentation, such as by distillation.

13. The process of any of paragraphs 1-12, wherein the fermentation product is an alcohol, preferably ethanol, especially fuel ethanol, potable ethanol and/or industrial ethanol.

14. The process of any of paragraphs 1-13, wherein the starch-containing starting material is whole grains.

15. The process of any of paragraphs 1-14, wherein the starch-containing material is derived from corn, wheat, barley, rye, milo, sago, cassava, manioc, tapioca, sorghum, rice or potatoes.

16. The process of any of paragraphs 1-15, wherein the fermenting organism is yeast, preferably a strain of *Saccharomyces*, especially a strain of *Saccharomyces cerevisiae.*

17. The process of any of paragraphs 1-16, wherein the alpha-amylase is a bacterial or fungal alpha-amylase.

18. The process of any of paragraphs 1-17, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

19. The process of paragraph 18, wherein the *Bacillus stearothermophilus* alpha-amylase or variant thereof is truncated, preferably to have around 491 amino acids.

20. The process of any of paragraphs 18 or 19, wherein the *Bacillus stearothermophilus* alpha-amylase has a double deletion of positions I181+G182 and optionally a N193F substitution, or deletion of R179+G180 (using SEQ ID NO: 1 for numbering).

21. The process of any of paragraphs 18-20 wherein the *Bacillus stearothermophilus* alpha-amylase has a substitution in position S242, preferably S242Q substitution.

22. The process of any of paragraphs 18-21, wherein the *Bacillus stearothermophilus* alpha-amylase has a substitution in position E188, preferably E188P substitution.

23. The process of any of paragraphs 1-22, wherein the alpha-amylase has a T½ (min) at pH 4.5, 85° C., 0.12 mM $CaCl_2$)) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

24. The process of any of paragraphs 1-23, wherein the alpha-amylase is selected from the group of *Bacillus stearothermophilus* alpha-amylase variants with the following mutations in addition to I181*+G182* and optionally N193F:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;

-continued

| |
|---|
| E129V + K177L + R179E + S242Q; |
| E129V + K177L + R179V + K220P + N224L + S242Q + Q254S; |
| K220P + N224L + S242Q + Q254S; |
| M284V; |
| V59A + Q89R + E129V + K177L + R179E + Q254S + M284V. |
| V59A + E129V + K177L + R179E + Q254S + M284V; |

25. The process of any of paragraphs 1-24, wherein the alpha-amylase is selected from the following group of *Bacillus stearothermophilus* alpha-amylase variants:

I181*+G182*+N193F+E129V+K177L+R179E;

I181*+G182*+N193F+V59A+Q89R+E129V+K177L+R179E+H208Y+K220P+N224L+Q254S

I181*+G182*+N193F+V59A+Q89R+E129V+K177L+R179E+Q254S+M284V;

I181*+G182*+N193F+V59A+E129V+K177L+R179E+Q254S+M284V and

I181*+G182*+N193F+E129V+K177L+R179E+K220P+N224L+S242Q+Q254S (using SEQ ID NO: 1 for numbering).

26. The process of any of paragraphs 1-25, wherein the protease with a thermostability value of more than 25% determined as Relative Activity at 80° C./70° C.

27. The process of any of paragraphs 1-26, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

28. The process of any of paragraphs 1-27, wherein the protease has a thermostability of between 20 and 50%, such as between 20 and 40%, such as 20 and 30% determined as Relative Activity at 80° C./70° C.

29. The process of any of paragraphs 1-28, wherein the protease has a thermostability between 50 and 115%, such as between 50 and 70%, such as between 50 and 60%, such as between 100 and 120%, such as between 105 and 115% determined as Relative Activity at 80° C./70° C.

30. The process of any of paragraphs 1-29, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

31. The process of any of paragraphs 1-30, wherein the protease has thermostability of between 10 and 50%, such as between 10 and 30%, such as between 10 and 25% determined as Relative Activity at 85° C./70° C.

32. The process of any of paragraphs 1-31, wherein the protease has a themostability above 60%, such as above 90%, such as above 100%, such as above 110% at 85° C. as determined using the Zein-BCA assay.

33. The process of any of paragraphs 1-32, wherein the protease has a themostability between 60-120, such as between 70-120%, such as between 80-120%, such as between 90-120%, such as between 100-120%, such as 110-120% at 85° C. as determined using the Zein-BCA assay.

34. The process of any of paragraphs 1-33, wherein the protease is of fungal origin.

35. The process of any of paragraphs 1-34, wherein the protease is a variant of the metallo protease derived from a strain of the genus *Thermoascus*, preferably a strain of *Thermoascus aurantiacus*, especially *Thermoascus aurantiacus* CGMCC No. 0670.

36. The process of any of paragraphs 1-35, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein mutations selected from the group of:

S5*+D79L+S87P+A112P+D142L;

D79L+S87P+A112P+T124V+D142L;

S5*+N26R+D79L+S87P+A112P+D142L;

N26R+T46R+D79L+S87P+A112P+D142L;

T46R+D79L+S87P+T116V+D142L;

D79L+P81R+S87P+A112P+D142L;

A27K+D79L+S87P+A112P+T124V+D142L;

D79L+Y82F+S87P+A112P+T124V+D142L;

D79L+Y82F+S87P+A112P+T124V+D142L;

D79L+S87P+A112P+T124V+A126V+D142L;

D79L+S87P+A112P+D142L;

D79L+Y82F+S87P+A112P+D142L;

S38T+D79L+S87P+A112P+A126V+D142L;

D79L+Y82F+S87P+A112P+A126V+D142L;

A27K+D79L+S87P+A112P+A126V+D142L;

D79L+S87P+N98C+A112P+G135C+D142L;

D79L+S87P+A112P+D142L+T141C+M161C;

S36P+D79L+S87P+A112P+D142L;

A37P+D79L+S87P+A112P+D142L;

S49P+D79L+S87P+A112P+D142L;

S50P+D79L+S87P+A112P+D142L;

D79L+S87P+D104P+A112P+D142L;

D79L+Y82F+S87G+A112P+D142L;

S70V+D79L+Y82F+S87G+Y97W+A112P+D142L;

D79L+Y82F+S87G+Y97W+D104P+A112P+D142L;

S70V+D79L+Y82F+S87G+A112P+D142L;

D79L+Y82F+S87G+D104P+A112P+D142L;

D79L+Y82F+S87G+A112P+A126V+D142L;

Y82F+S87G+S70V+D79L+D104P+A112P+D142L;

Y82F+S87G+D79L+D104P+A112P+A126V+D142L;

A27K+D79L+Y82F+S87G+D104P+A112P+A126V+D142L;

A27K+Y82F+S87G+D104P+A112P+A126V+D142L;

A27K+D79L+Y82F+D104P+A112P+A126V+D142L;

A27K+Y82F+D104P+A112P+A126V+D142L;

A27K+D79L+S87P+A112P+D142L; and

D79L+S87P+D142L.

37. The process of any of paragraphs 1-36, wherein the protease is a variant of the metallo protease disclosed as the mature part of SEQ ID NO. 2 disclosed in WO 2003/048353 or the mature part of SEQ ID NO: 1 in WO 2010/008841 or SEQ ID NO: 3 herein with the following mutations:

D79L+S87P+A112P+D142L:

D79L+S87P+D142L; or

A27K+D79L+Y82F+S87G+D104P+A112P+A126V+D142L.

38. The process of any of paragraphs 1-37, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

39. The process of any of paragraphs 1-38, wherein the protease variant of the *Thermoascus aurantiacus* protease shown in SEQ ID NO: 3 is one of the following:

D79L S87P D142L
D79L S87P A112P D142L
D79L Y82F S87P A112P D142L
S38T D79L S87P A112P A126V D142L
D79L Y82F S87P A112P A126V D142L
A27K D79L S87P A112P A126V D142L
S49P D79L S87P A112P D142L
S50P D79L S87P A112P D142L
D79L S87P D104P A112P D142L
D79L Y82F S87G A112P D142L
S70V D79L Y82F S87G Y97W A112P D142L
D79L Y82F S87G Y97W D104P A112P D142L
S70V D79L Y82F S87G A112P D142L
D79L Y82F S87G D104P A112P D142L
D79L Y82F S87G A112P A126V D142L
Y82F S87G S70V D79L D104P A112P D142L
Y82F S87G D79L D104P A112P A126V D142L
A27K D79L Y82F S87G D104P A112P A126V D142L

40. The process of any of paragraphs 1-39, wherein the protease is of bacterial origin.

41. The process of any of paragraphs 1-40, wherein the protease is derived from a strain of *Pyrococcus*, preferably a strain of *Pyrococcus furiosus*.

42. The process of any of paragraphs 1-41, wherein the protease is the one shown in SEQ ID NO: 1 in U.S. Pat. No. 6,358,726, SEQ ID NO: 13 herein or SEQ ID NO: 29 herein.

43. The process of any of paragraphs 1-42, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726 or SEQ ID NO: 13 herein.

44. The process of any of paragraphs 1-43, wherein a carbohydrate-source generating enzyme is present and/or added during liquefaction step i), preferably a glucoamylase.

45. The process of any of paragraphs 1-44, wherein the carbohydrate-source generating enzyme present and/or added during liquefaction step i) is a glucoamylase having a heat stability at 85° C., pH 5.3, of at least 20%, such as at least 30%, preferably at least 35%.

46. The process of any of paragraphs 44-45, wherein the carbohydrate-source generating enzyme is a glucoamylase having a relative activity pH optimum at pH 5.0 of at least 90%, preferably at least 95%, preferably at least 97%.

47. The process of any of paragraphs 44-46, wherein the carbohydrate-source generating enzyme is a glucoamylase having a pH stability at pH 5.0 of at least at least 80%, at least 85%, at least 90%.

48. The process of any of paragraphs 44-47, wherein the carbohydrate-source generating enzyme present and/or added during liquefaction step i) is a glucoamylase, preferably derived from a strain of the genus *Penicillium*, especially a strain of *Penicillium oxalicum* disclosed as SEQ ID NO: 2 in WO 2011/127802 or SEQ ID NOs: 9 or 14 herein.

49. The process of paragraph 44-48, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

50. The composition of any of paragraphs 44-49, wherein the carbohydrate-source generating enzyme is a variant of the glucoamylase derived from a strain of *Penicillium oxalicum* disclosed as SEQ ID NO: 2 in WO 2011/127802 having a K79V substitution (using the mature sequence shown in SEQ ID NO: 14 for numbering).

51. The process of any of paragraphs 44-50, further wherein a glucoamylase is present and/or added during saccharification and/or fermentation.

52. The process of any of paragraphs 1-51, wherein the glucoamylase present and/or added during saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*, such as a strain of *Gloeophyllum sepiarium* or *Gloeophyllum trabeum*, such as one disclosed in WO 2011/068803 as any of SEQ ID NOs: 2, 4, 6, 8, 10, 12, 14 or 16, preferably SEQ ID NO: 2 in WO 2011/068803, or a strain of the *Nigrofomes*.

53. The process of paragraph 52, wherein the glucoamylase present and/or added during saccharification and/or fermentation is a blend comprising *Talaromyces emersonii* glucoamylase disclosed in WO 99/28448 as SEQ ID NO: 7 and *Trametes cingulata* glucoamylase disclosed in WO 06/069289.

54. The process of paragraphs 52 or 53 wherein the glucoamylase present and/or added during saccharification and/or fermentation is a blend comprising *Talaromyces emersonii* glucoamylase disclosed in WO 99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290.

55. The process of any of paragraphs 52-54, wherein the glucoamylase present and/or added during saccharification and/or fermentation is a blend comprising *Talaromyces emersonii* glucoamylase disclosed in WO99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290.

56. The process of paragraph 52, wherein the glucoamylase present and/or added during saccharification and/or fermentation is a blend comprising *Gloeophyllum sepiarium* glucoamylase shown as SEQ ID NO: 2 in WO 2011/068803 and *Rhizomucor pusillus* with an *Aspergillus niger* glucoamylase linker and starch-binding domain (SBD), disclosed SEQ ID NO: 3 in WO 2013/006756 with the following substitutions: G128D+D143N.

57. The process of any of paragraphs 1-56, further wherein a pullulanase is present during liquefaction and/or saccharification.

58. The process of any of paragraphs 1-57, comprising the steps of:

i) liquefying the starch-containing material at a temperature above the initial gelatinization temperature using: an alpha-amylase derived from *Bacillus stearothermophilus;* optionally a protease having a thermostability value of more than 20% determined as Relative Activity at 80° C./70° C., preferably derived from *Pyrococcus furiosus* and/or *Thermoascus aurantiacus*; and optionally a *Penicillium oxalicum* glucoamylase;

ii) saccharifying using a glucoamylase enzyme;

iii) fermenting using a fermenting organism;

wherein a cellulolytic composition is present or added during fermentation or simultaneous saccharification and fermentation.

59. A process of paragraphs 1-58, comprising the steps of:

i) liquefying the starch-containing material at a temperature above the initial gelatinization temperature using:

an alpha-amylase, preferably derived from *Bacillus stearothermophilus*, having a T½ (min) at pH 4.5, 85° C., 0.12 mM $CaCl_2$) of at least 10;

optionally a protease, preferably derived from *Pyrococcus furiosus* and/or *Thermoascus aurantiacus*, having a thermostability value of more than 20% determined as Relative Activity at 80° C./70° C.;

optionally a *Penicillium oxalicum* glucoamylase;

ii) saccharifying using a glucoamylase enzyme;

iii) fermenting using a fermenting organism;

wherein a cellulolytic composition is present or added during fermentation or simultaneous saccharification and fermentation.

60. A process of paragraphs 1-59, comprising the steps of:

i) liquefying the starch-containing material at a temperature between 80-90° C.:

an alpha-amylase, preferably derived from *Bacillus stearothermophilus*, having a T½ (min) at pH 4.5, 85° C., 0.12 mM $CaCl_2$) of at least 10;

optionally a protease, preferably derived from *Pyrococcus furiosus* and/or *Thermoascus aurantiacus*, having a thermostability value of more than 20% determined as Relative Activity at 80° C./70° C.;

optionally a *Penicillium oxalicum* glucoamylase;

ii) saccharifying using a glucoamylase enzyme;

iii) fermenting using a fermenting organism;

wherein a cellulolytic composition is present and/or added during fermentation or simultaneous saccharification and fermentation.

61. A process of paragraphs 1-60, comprising the steps of:

i) liquefying the starch-containing material at a temperature above the initial gelatinization temperature using:

an alpha-amylase derived from *Bacillus stearothermophilus* having a double deletion I181+G182 and optional substitution N193F; and optionally further one of the following set of substitutions:

E129V+K177L+R179E;

V59A+Q89R+E129V+K177L+R179E+H208Y+K220P+N224L+Q254S:

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering).

optionally a protease having a thermostability value of more than 20% determined as Relative Activity at 80° C./70° C., preferably derived from *Pyrococcus furiosus* and/or *Thermoascus aurantiacus*; and optionally a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition is present and/or added during fermentation or simultaneous saccharification and fermentation.

62. A process of paragraphs 1-61, comprising the steps of:

i) liquefying the starch-containing material at a temperature between 80-90° ° C. using:

an alpha-amylase derived from *Bacillus stearothermophilus* having a double deletion I181+G182 and optional substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering), optionally a protease having a thermostability value of more than 20% determined as Relative Activity at 80° C./70° C., preferably derived from *Pyrococcus furiosus* and/or *Thermoascus aurantiacus;* optionally a pullulanase optionally a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition is present and/or added during fermentation or simultaneous saccharification and fermentation.

63. The process of any of paragraphs 1-62, comprising the steps of:

i) liquefying the starch-containing material at a temperature above the initial gelatinization temperature using:

an alpha-amylase derived from *Bacillus stearothermophilus;* optionally a protease having a thermostability value of more than 20% determined as Relative Activity at 80° C./70° C., preferably derived from *Pyrococcus furiosus* and/or *Thermoascus aurantiacus*; and optionally a pullulanase;

optionally a *Penicillium oxalicum* glucoamylase;

ii) saccharifying using a glucoamylase enzyme;

iii) fermenting using a fermenting organism wherein a cellulolytic composition is present and/or added during fermentation or simultaneous saccharification and fermentation.

64. A process of paragraphs 1-63, comprising the steps of:
i) liquefying the starch-containing material at a temperature above the initial gelatinization temperature using:
an alpha-amylase, preferably derived from *Bacillus stearothermophilus*, having a T½ (min) at pH 4.5, 85° ° C., 0.12 mM $CaCl_2$) of at least 10;
optionally a protease, preferably derived from *Pyrococcus furiosus* and/or *Thermoascus aurantiacus*, having a thermostability value of more than 20% determined as Relative Activity at 80° C./70° C.;
optionally a pullulanase;
optionally a *Penicillium oxalicum* glucoamylase
ii) saccharifying using a glucoamylase enzyme;
iii) fermenting using a fermenting organism;
wherein a cellulolytic composition is present and/or added during fermentation or simultaneous saccharification and fermentation.

65. A process of paragraphs 1-64, comprising the steps of:
i) liquefying the starch-containing material at a temperature between 80-90° C.:
an alpha-amylase, preferably derived from *Bacillus stearothermophilus*, having a T½ (min) at pH 4.5, 85° C., 0.12 mM $CaCl_2$) of at least 10;
optionally a optionally a protease, preferably derived from *Pyrococcus furiosus* or *Thermoascus aurantiacus*, having a thermostability value of more than 30% determined as Relative Activity at 80° C./70° C.;
optionally a pullulanase;
ii) saccharifying using a glucoamylase enzyme;
iii) fermenting using a fermenting organism;
wherein a cellulolytic composition is present and/or added during fermentation or simultaneous saccharification and fermentation.

66. A process of paragraphs 1-65, comprising the steps of:
i) liquefying the starch-containing material at a temperature above the initial gelatinization temperature using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V:
V59A+E129V+K177L+R179E+Q254S+M284V
E129V+K177L+R179E+K220P+N224L+S242Q+Q254S (using SEQ ID NO: 1 herein for numbering);
optionally a protease having a thermostability value of more than 20% determined as Relative Activity at 80° C./70° C., preferably derived from *Pyrococcus furiosus* and/or *Thermoascus aurantiacus*; and
optionally a pullulanase;
optionally a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase enzyme;
iii) fermenting using a fermenting organism;
wherein a cellulolytic composition is present and/or added during fermentation or simultaneous saccharification and fermentation.

67. A process of paragraphs 1-66, comprising the steps of:
i) liquefying the starch-containing material at a temperature between 80-90° C. using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V
E129V+K177L+R179E+K220P+N224L+S242Q+Q254S (using SEQ ID NO: 1 herein for numbering).
optionally a protease having a thermostability value of more than 20% determined as Relative Activity at 80° C./70° C., preferably derived from *Pyrococcus furiosus* and/or *Thermoascus aurantiacus*; and
optionally a pullulanase;
optionally a *Penicillium oxalicum* glucoamylase shown in SEQ ID NO: 14 having substitutions selected from the group of:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase enzyme;
iii) fermenting using a fermenting organism;
wherein a cellulolytic composition is present and/or added during fermentation or simultaneous saccharification and fermentation.

68. A process of any of paragraphs 1-67, comprising the steps of:
i) liquefying the starch-containing material at a temperature between 80-90° ° C. at a pH between 5.0 and 6.5 using:
an alpha-amylase derived from *Bacillus stearothermophilus* having a double deletion I181+G182 and optional substitution N193F; and optionally further one of the following set of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V
E129V+K177L+R179E+K220P+N224L+S242Q+Q254S (using SEQ ID NO: 1 herein for numbering).
a protease derived from *Pyrococcus furiosus*, preferably the one shown in SEQ ID NO: 13 herein or SEQ ID NO: 29 here;
a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

ii) saccharifying using a glucoamylase enzyme;

iii) fermenting using a fermenting organism;

wherein a cellulolytic composition, such as a *Trichoderma reesei* cellulolytic composition, is present and/or added during fermentation or simultaneous saccharification and fermentation, in particular a *Trichoderma reesei* cellulolytic composition comprising one or more polypeptides selected from the group consisting of:

GH61 polypeptide having cellulolytic enhancing activity, beta-glucosidase;

Cellobiohydrolase I;

Cellobiohydrolase II;

or a mixture of two, three, or four thereof.

69. The process of any of paragraphs 57-68, wherein pullulanase present and/or added during liquefaction step i) is a family GH57 pullulanase, wherein the pullulanase preferably includes an X47 domain as disclosed in WO 2011/087836.

70. The process of any of paragraphs 57-69, wherein the pullulanase is derived from a strain from the genus *Thermococcus*, including *Thermococcus litoralis* and *Thermococcus hydrothermalis* or a hybrid thereof.

71. The process of any of paragraphs 57-70, wherein the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

72. The process of any of paragraphs 57-71, wherein the *Bacillus stearothermophilus* alpha-amylase (SEQ ID NO: 1 herein) is the mature alpha-amylase or corresponding mature alpha-amylases having at least 80% identity, at least 90% identity, at least 95% identity at least 96% identity at least 97% identity at least 99% identity to the SEQ ID NO: 1.

73. The process of any of paragraphs 41-72, wherein the *Pyrococcus furiosus* protease (SEQ ID NO: 13 herein or SEQ ID NO: 29 herein) and/or *Thermoascus aurantiacus* protease (SEQ ID NO: 3) is the mature protease or corresponding mature protease having at least 80% identity, at least 90% identity, at least 95% identity at least 96% identity at least 97% identity at least 99% identity to the SEQ ID NO: 13, SEQ ID NO: 29 herein, or SEQ ID NO: 3 herein, respectively.

74. The process of any of paragraphs 48-73, wherein the *Penicillium oxalicum* glucoamylase (SEQ ID NO: 14 herein) is the mature glucoamylase or corresponding mature glucoamylase having at least 80% identity, at least 90% identity, at least 95% identity at least 96% identity at least 97% identity at least 99% identity to the SEQ ID NO: 14 herein.

75. The process of paragraphs 1-74, wherein the cellulolytic composition is derived from a strain of *Trichoderma*, in particular *Trichoderma reesei*, or a strain of *Humicola*, in particular *Humicola insolens*, or a strain of *Chrysosporium*, in particular *Chrysosporium lucknowense*.

76. The process of paragraphs 1-75, wherein the cellulolytic composition comprises a beta-glucosidase, a cellobiohydrolase and an endoglucanase.

77. The process of any of paragraphs 1-76, wherein the cellulolytic composition comprising one or more polypeptides selected from the group consisting of:

GH61 polypeptide having cellulolytic enhancing activity, beta-glucosidase;

Cellobiohydrolase I;

Cellobiohydrolase II;

or a mixture of two, three, or four thereof.

78. The process of any of paragraphs 1-77, wherein the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as the one disclosed in WO 2005/047499 or SEQ ID NO: 22 herein or an *Aspergillus fumigatus* beta-glucosidase variant disclosed in WO 2012/044915 or a strain of the genus a strain *Penicillium*, such as a strain of the *Penicillium brasilianum* disclosed in WO 2007/019442, or a strain of the genus *Trichoderma*, such as a strain of *Trichoderma reesei.*

79. The process of any one of paragraphs 1-78, wherein the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 23 herein.

80. The process of any one of paragraphs 1-79, wherein the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 2 in WO 2011/057140 or SEQ ID NO: 24 herein, or a strain of the genus *Trichoderma*, such as a strain of *Trichoderma reesei.*

81. The process of any one of paragraphs 1-80, wherein the cellulolytic composition comprises a cellobiohydrolase II (CBH II, such as one derived from a strain of the genus *Aspergillus*, such as a strain of *Aspergillus fumigatus*; such as the one disclosed as SEQ ID NO: 25 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris.*

82. The process of any one of paragraphs 1-81, wherein the cellulolytic composition comprises a GH61 polypeptide having cellulolytic enhancing activity and a beta-glucosidase.

83. The process of any one of paragraphs 1-82, wherein the cellulolytic composition comprises a GH61 polypeptide having cellulolytic enhancing activity and a beta-glucosidase.

84. The process of any one of paragraphs 1-83, wherein the cellulolytic composition comprises a GH61 polypeptide having cellulolytic enhancing activity, a beta-glucosidase, and a CBHI.

85. The process of any one of paragraphs 1-84, wherein the cellulolytic composition comprises a GH61 polypeptide having cellulolytic enhancing activity, a beta-glucosidase, a CBHI, and a CBHII.

86. The process of any of paragraphs 1-85, wherein the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

87. The process of any of paragraphs 1-86, wherein the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 22 herein.

88. The process of any one of paragraphs 1-87, wherein the cellulolytic composition is a *Trichoderma reesei* cellulolytic enzyme composition further comprising *Penicillium emersonii GH*61A polypeptide having cellulolytic enhancing activity disclosed in WO 2011/041397 (SEQ ID NO: 23 herein) and *Aspergillus fumigatus* beta-glucosidase (SEQ ID NO: 2 of WO 2005/047499) or SEQ ID NO: 22 herein or a variant thereof with the following substitutions: F100D, S283G, N456E, F512Y.

89. The process of any of paragraphs 1-88, wherein the cellulolytic composition comprises one or more of the following components (i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof; and (iv) a *Penicillium* sp. GH61 polypeptide having cellulolytic enhancing activity; or homologs thereof.

90. The process of any of paragraphs 1-89, wherein the cellulolytic composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

91. An enzyme composition comprising:

an alpha-amylase;

optionally a protease having a thermostability value of more than 20% determined as Relative Activity at 80° C./70° C.;

optionally a pullulanase; and optionally a carbohydrate-source generating enzyme.

92 The composition of paragraph 91, wherein the alpha-amylase is a bacterial or fungal alpha-amylase.

93. The composition of any of paragraphs 91-92, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

94. The composition of paragraph 93, wherein the *Bacillus stearothermophilus* alpha-amylase or variant thereof is truncated, preferably to have around 491 amino acids.

95. The composition of any of paragraphs 91-94, wherein the *Bacillus stearothermophilus* alpha-amylase has a double deletion of positions I181+G182, and optionally a N193F substitution, or deletion of R179+G180 (using SEQ ID NO: 1 for numbering).

96. The composition of any of paragraphs 91-95, wherein the *Bacillus stearothermophilus* alpha-amylase has a substitution in position S242, preferably S242Q substitution.

97. The composition of any of paragraphs 91-96, wherein the *Bacillus stearothermophilus* alpha-amylase has a substitution in position E188, preferably E188P substitution.

98. The composition of any of paragraphs 91-97, wherein the alpha-amylase has a T½ (min) at pH 4.5, 85° C., 0.12 mM $CaCl_2$)) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

99. The composition of any of paragraphs 91-98, wherein the alpha-amylase is selected from the group of *Bacillus stearothermophilus* alpha-amylase variants:

I181*+G182*+N193F+E129V+K177L+R179E;

I181*+G182*+N193F+V59A+Q89R+E129V+K177L+R179E+H208Y+K220P+N224L+Q254S:

I181*+G182*+N193F+V59A+Q89R+E129V+K177L+R179E+Q254S+M284V;

I181*+G182*+N193F+V59A+E129V+K177L+R179E+Q254S+M284V; and

I181*+G182*+N193F+E129V+K177L+R179E+K220P+N224L+S242Q+Q254S.

100. The composition of any of paragraphs 91-99, wherein the protease with a thermostability value of more than 25% determined as Relative Activity at 80° C./70° C.

101. The composition of any of paragraphs 91-100, wherein the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

102. The composition of any of paragraphs 91-101, wherein the protease has a thermostability of between 20 and 50%, such as between 20 and 40%, such as 20 and 30% determined as Relative Activity at 80° C./70° C.

103. The composition of any of paragraphs 91-102, wherein the protease has a thermostability between 50 and 115%, such as between 50 and 70%, such as between 50 and 60%, such as between 100 and 120%, such as between 105 and 115% determined as Relative Activity at 80° C./70° C.

104. The composition of any of paragraphs 91-103, wherein the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

105. The composition of any of paragraphs 91-10486-99, wherein the protease has thermostability of between 10 and 50%, such as between 10 and 30%, such as between 10 and 25% determined as Relative Activity at 85° C./70° C.

106. The composition of any of paragraphs 91-105, wherein the protease has a themostability above 60%, such as above 90%, such as above 100%, such as above 110% at 85° C. as determined using the Zein-BCA assay.

107. The composition of any of paragraphs 91-106, wherein the protease has a themostability between 60-120, such as between 70-120%, such as between 80-120%, such as between 90-120%, such as between 100-120%, such as 110-120% at 85° C. as determined using the Zein-BCA assay.

108. The composition of any of paragraphs 91-107, wherein the protease is of fungal origin.

109. The composition of any of paragraphs 91-108, wherein the protease is a variant of the metallo protease derived from a strain of the genus *Thermoascus*, preferably a strain of *Thermoascus aurantiacus*, especially *Thermoascus aurantiacus* CGMCC No. 0670.

110. The composition of any of paragraphs 91-109, wherein the protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein with the following mutations:

D79L+S87P+A112P+D142L:
D79L+S87P+D142L; or
A27K+D79L+Y82F+S87G+D104P+A112P+A126V+D142L.

111. The composition of any of paragraphs 91-110, wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

112. The composition of any of paragraphs 91-111, wherein the protease variant of the *Thermoascus aurantiacus* protease shown in SEQ ID NO: 3 herein is one of the following:

D79L S87P D142L;
D79L S87P A112P D142L;
D79L Y82F S87P A112P D142L;
S38T D79L S87P A112P A126V D142L;
D79L Y82F S87P A112P A126V D142L;
A27K D79L S87P A112P A126V D142L;
S49P D79L S87P A112P D142L;
S50P D79L S87P A112P D142L;
D79L S87P D104P A112P D142L;
D79L Y82F S87G A112P D142L;
S70V D79L Y82F S87G Y97W A112P D142L;
D79L Y82F S87G Y97W D104P A112P D142L;
S70V D79L Y82F S87G A112P D142L;
D79L Y82F S87G D104P A112P D142L;
D79L Y82F S87G A112P A126V D142L;
Y82F S87G S70V D79L D104P A112P D142L;
Y82F S87G D79L D104P A112P A126V D142L;
A27K D79L Y82F S87G D104P A112P A126V D142L.

113. The composition of any of paragraphs 91-112, wherein the protease is of bacterial origin.

114. The composition of any of paragraphs 91-113, wherein the protease is derived from a strain of *Pyrococcus*, preferably a strain of *Pyrococcus furiosus.*

115. The composition of any of paragraphs 91-114, wherein the protease is the one shown in SEQ ID NO: 1 in U.S. Pat. No. 6,358,726, SEQ ID NO: 13 herein or SEQ ID NO: 29 herein.

116. The composition of any of paragraphs 91-115, wherein the protease is one having at least 80%, such as at least 85%, such as at least 90%, such as at least 95%, such as at least 96%, such as at least 97%, such as at least 98%, such as at least 99% identity to in SEQ ID NO: 1 in U.S. Pat. No. 6,358,726, SEQ ID NO: 13 herein or SEQ ID NO: 29 herein.

117. The composition of any of paragraphs 91-116, wherein a carbohydrate-source generating enzyme is a glucoamylase.

118. The composition of any of paragraphs 91-117, wherein the carbohydrate-source generating enzyme is a glucoamylase having a heat stability at 85° C., pH 5.3, of at least 20%, such as at least 30%, preferably at least 35%.

119. The composition of any of paragraphs 91-118, wherein the carbohydrate-source generating enzyme is a glucoamylase having a relative activity pH optimum at pH 5.0 of at least 90%, preferably at least 95%, preferably at least 97%.

120. The composition of any of paragraphs 91-120, wherein the carbohydrate-source generating enzyme is a glucoamylase having a pH stability at pH 5.0 of at least at least 80%, at least 85%, at least 90%.

121. The composition of any of paragraphs 91-120, wherein the carbohydrate-source generating enzyme is a glucoamylase, preferably derived from a strain of the genus *Penicillium*, especially a strain of *Penicillium oxalicum* disclosed as SEQ ID NO: 2 in WO 2011/127802 or SEQ ID NOs: 9 or 14 herein.

122. The composition of any of paragraphs 91-121, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

123. The composition of any of paragraphs 91-122, wherein the carbohydrate-source generating enzyme is a variant of the glucoamylase derived from a strain of *Penicillium oxalicum* disclosed as SEQ ID NO: 2 in WO 2011/127802 having a K79V substitution (using the mature sequence shown in SEQ ID NO: 14 for numbering).

124. The composition of any of paragraphs 91-123, further comprising a glucoamylase.

125. The composition of any of paragraphs 91-124, further comprising a pullulanase.

126. The composition of any of paragraphs 91-125, comprising an alpha-amylase derived from *Bacillus stearothermophilus;*
optionally a protease having a thermostability value of more than 20% determined as Relative Activity at 80° C./70° C. derived from *Pyrococcus furiosus* or *Thermoascus aurantiacus;*
optionally a pullulanase;
optionally a glucoamylase derived from *Penicillium oxalicum.*

127. The composition of any of paragraphs 91-126, comprising an alpha-amylase derived from *Bacillus stearothermophilus;*
a protease having a thermostability value of more than 20% determined as Relative Activity at 80° C./70° C. derived from *Pyrococcus furiosus* or *Thermoascus aurantiacus;*
optionally a pullulanase;
a glucoamylase derived from *Penicillium oxalicum.*

128. The composition of any of paragraphs 91-127, comprising an alpha-amylase, preferably derived from *Bacillus stearothermophilus*, having a T½ (min) at pH 4.5, 85° C., 0.12 mM $CaCl_2$) of at least 10;
optionally a protease, preferably derived from *Pyrococcus furiosus* or *Thermoascus aurantiacus*, having a thermostability value of more than 20% determined as Relative Activity at 80° C./70° C.;
optionally a pullulanase;

optionally a glucoamylase derived from *Penicillium oxalicum.*

129. The composition of any of paragraphs 91-128, comprising an alpha-amylase derived from *Bacillus stearothermophilus* having a double deletion I181+G182 and substitution N193F; and optionally further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V;

E129V+K177L+R179E+K220P+N224L+S242Q+Q254S (using SEQ ID NO: 1 herein for numbering);

optionally a protease having a thermostability value of more than 20% determined as Relative Activity at 80° C./70° C. derived from *Pyrococcus furiosus* and/or *Thermoascus aurantiacus;* optionally a pullulanase;

optionally a *Penicillium oxalicum* glucoamylase in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering).

130. The composition of any of paragraphs 91-129 comprises:

an alpha-amylase derived from *Bacillus stearothermophilus* having a double deletion I181+G182+N193F; and further one of the following set of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V

E129V+K177L+R179E+K220P+N224L+S242Q+Q254S (using SEQ ID NO: 1 herein for numbering).

a protease derived from *Pyrococcus furiosus*, preferably the one shown in SEQ ID NO: 13 herein or SEQ ID NO: 29 herein;

a *Penicillium oxalicum* glucoamylase shown in SEQ ID NO: 14 having substitutions selected from the group of:

K79V;

K79V+P11F+T65A+Q327F; or

K79V+P2N+P4S+P11F+T65A+Q327F; or

K79V+P11F+D26C+K33C+T65A+Q327F; or

K79V+P2N+P4S+P11F+T65A+Q327W+E501V+Y504T; or

K79V+P2N+P4S+P11F+T65A+Q327F+E501V+Y504T; or

K79V+P11F+T65A+Q327W+E501V+Y504T (using SEQ ID NO: 14 for numbering);

131. The compositions of any of paragraphs 91-130, comprising an alpha-amylase derived from *Bacillus stearothermophilus* having a double deletion I181*+G182*+N193F+V59A+Q89R+E129V+K177L+R179E+Q254S+M284V (using SEQ ID NO: 1 herein for numbering).

a protease derived from *Pyrococcus furiosus* preferably the one shown in SEQ ID NO: 13 herein or SEQ ID NO: 29 herein;

a *Penicillium oxalicum* glucoamylase shown in SEQ ID NO: 14 having substitutions selected from the group of:

K79V+P11F+T65A+Q327F

K79V+P2N+P4F+P11F+T65A+Q327F (using SEQ ID NO: 14 for numbering).

132. The composition of any of paragraphs 126-131, wherein the pullulanase is a family GH57 pullulanase, wherein the pullulanase preferably includes an X47 domain as disclosed in WO 2011/087836.

133. The composition of any of paragraphs 126-132, wherein the pullulanase is derived from a strain from the genus *Thermococcus*, including *Thermococcus litoralis* and *Thermococcus hydrothermalis* or a hybrid thereof.

134. The composition of any of paragraphs 126-133, wherein the pullulanase is the truncated *Thermococcus hydrothermalis* pullulanase at site X4 or a *T. hydrothermalis/T. litoralis* hybrid enzyme with truncation site X4 disclosed in WO 2011/087836 or shown in SEQ ID NO: 12 herein.

135. The composition of any of paragraphs 126-134, wherein the *Bacillus stearothermophilus* alpha-amylase (SEQ ID NO: 1 herein), or a variant thereof, is the mature alpha-amylase or corresponding mature alpha-amylases having at least 80% identity, at least 90% identity, at least 95% identity at least 96% identity at least 97% identity at least 99% identity to SEQ ID NO: 1.

136. The composition of any of paragraphs 91-135, wherein the *Pyrococcus furiosus* protease (SEQ ID NO: 13 herein or SEQ ID NO: 29 herein) and/or *Thermoascus aurantiacus* protease (SEQ ID NO: 3 herein), or a variant thereof, is the mature protease or corresponding mature protease having at least 80% identity, at least 90% identity, at least 95% identity at least 96% identity at least 97% identity at least 99% identity to SEQ ID NO: 13 herein or SEQ ID NO: 29 herein, or SEQ ID NO: 3, respectively.

137. The composition of any of paragraphs 91-136, wherein the *Penicillium oxalicum* glucoamylase (SEQ ID NO: 14 herein), or a variant thereof, is the mature glucoamylase or corresponding mature glucoamylase having at least 80% identity, at least 90% identity, at least 95% identity at least 96% identity at least 97% identity at least 99% identity to the SEQ ID NO: 14 herein.

The invention claimed is:

1. A cellulolytic composition comprising:

(a) a beta-glucosidase having an amino acid sequence that is at least 85% identical to the amino acid sequence of SEQ ID NO: 22 and having the substitutions F100D, S283G, N456E and F512Y; and (b) a cellobiohydrolase I ("CBHI") having an amino acid sequence that is at least 85% identical to the amino acid sequence of SEQ ID NO: 24; and (c) a cellobiohydrolase II ("CBHII") having an amino acid sequence that is at least 85% identical to the amino acid sequence of SEQ ID NO: 25; and a glucoamylase.

2. The composition of claim 1, wherein the composition is derived from a strain of *Trichoderma*.

3. The composition of claim 1, wherein the composition is derived from a strain of *Trichoderma reesei*.

4. The composition of claim 1, wherein the beta-glucosidase has an amino acid sequence that is at least 90% identical to the amino acid sequence of SEQ ID NO: 22.

5. The composition of claim 1, wherein the beta-glucosidase has an amino acid sequence that is at least 95% identical to the amino acid sequence of SEQ ID NO: 22.

6. The composition of claim 1, further comprising a GH61 polypeptide having cellulolytic enhancing activity.

7. The composition of claim 6, wherein the GH61 polypeptide has an amino acid sequence that is at least 85% identical to the amino acid sequence of SEQ ID NO: 23.

8. The composition of claim 6, wherein the GH61 polypeptide has an amino acid sequence that is at least 90% identical to the amino acid sequence of SEQ ID NO: 23.

9. The composition of claim 6, wherein the GH61 polypeptide has an amino acid sequence that is at least 95% identical to the amino acid sequence of SEQ ID NO: 23.

10. The composition of claim 1, wherein the CBHI has an amino acid sequence that is at least 90% identical to the amino acid sequence of SEQ ID NO: 24.

11. The composition of claim 1, wherein the CBHI has an amino acid sequence that is at least 95% identical to the amino acid sequence of SEQ ID NO: 24.

12. The cellulolytic composition of claim 1, wherein the CBHII has an amino acid sequence that is at least 90% identical to the amino acid sequence of SEQ ID NO: 25.

13. The cellulolytic composition of claim 1, wherein the CBHII has an amino acid sequence that is at least 95% identical to the amino acid sequence of SEQ ID NO: 25.

14. A process for producing ethanol from corn, the process comprising:

(i) liquefying the corn at a temperature above the initial gelatinization temperature using a thermostable alpha-amylase and a thermostable protease;

(ii) saccharifying using a glucoamylase; and (iii) fermenting with a yeast, wherein a cellulolytic composition is present or added during saccharifying step (ii) and/or fermenting step (iii), wherein the cellulolytic composition comprises:

(a) a beta-glucosidase having an amino acid sequence that is at least 85% identical to the amino acid sequence of SEQ ID NO: 22 and having the substitutions F100D, S283G, N456E and F512Y; and (b) a cellobiohydrolase I ("CBHI") having an amino acid sequence that is at least 85% identical to the amino acid sequence of SEQ ID NO: 24; and (c) a cellobiohydrolase II ("CBHII") having an amino acid sequence that is at least 85% identical to the amino acid sequence of SEQ ID NO: 25.

15. The process of claim 14, wherein the composition is derived from a strain of *Trichoderma.*

16. The process of claim 14, wherein the composition is derived from a strain of *Trichoderma reesei.*

17. The process of claim 14, wherein the beta-glucosidase has an amino acid sequence that is at least 90% identical to the amino acid sequence of SEQ ID NO: 22.

18. The process of claim 14, wherein the beta-glucosidase has an amino acid sequence that is at least 95% identical to the amino acid sequence of SEQ ID NO: 22.

19. The process of claim 14, wherein the cellulolytic composition further comprises a GH61 polypeptide having cellulolytic enhancing activity.

20. The process of claim 19, wherein the GH61 polypeptide has an amino acid sequence that is at least 85% identical to the amino acid sequence of SEQ ID NO: 23.

21. The process of claim 19, wherein the GH61 polypeptide has an amino acid sequence that is at least 90% identical to the amino acid sequence of SEQ ID NO: 23.

22. The process of claim 19, wherein the GH61 polypeptide has an amino acid sequence that is at least 95% identical to the amino acid sequence of SEQ ID NO: 23.

23. The process of claim 19, wherein the CBHI has an amino acid sequence that is at least 90% identical to the amino acid sequence of SEQ ID NO: 24.

24. The process of claim 19, wherein the CBHI has an amino acid sequence that is at least 95% identical to the amino acid sequence of SEQ ID NO: 24.

25. The process of claim 19, wherein the CBHII has an amino acid sequence that is at least 90% identical to the amino acid sequence of SEQ ID NO: 25.

26. The process of claim 19, wherein the CBHII has an amino acid sequence that is at least 95% identical to the amino acid sequence of SEQ ID NO: 25.

27. The composition of claim 1, wherein the glucoamylase comprises a blend comprising a *Talaromyces emersonii* glucoamylase, a *Trametes* cingulate glucoamylase, and a *Rhizomucor pusillus* alpha-amylase with *Aspergillus niger* glucoamylase linker and starch binding domain (SBD).

* * * * *